US008968996B2

(12) United States Patent
Stinchcomb et al.

(10) Patent No.: US 8,968,996 B2
(45) Date of Patent: Mar. 3, 2015

(54) COMPOSITIONS AND METHODS FOR RAPID IMMUNIZATION AGAINST DENGUE VIRUS

(75) Inventors: Dan T. Stinchcomb, Fort Collins, CO (US); Jorge E. Osorio, Mount Horeb, WI (US); Charalambos D. Partidos, Chicago, IL (US); Joseph N. Brewoo, Madison, WI (US)

(73) Assignee: Takeda Vaccines, Inc., Deerfield, IL (US)

( * ) Notice: Subject to any disclaimer, the term of this patent is extended or adjusted under 35 U.S.C. 154(b) by 60 days.

(21) Appl. No.: 13/492,884

(22) Filed: Jun. 10, 2012

(65) Prior Publication Data
US 2013/0149338 A1  Jun. 13, 2013

Related U.S. Application Data

(63) Continuation-in-part of application No. 12/790,511, filed on May 28, 2010.

(60) Provisional application No. 61/183,020, filed on Jun. 1, 2009.

(51) Int. Cl.
| | | |
|---|---|---|
| *C12Q 1/70* | (2006.01) | |
| *A61K 39/295* | (2006.01) | |
| *A61K 39/12* | (2006.01) | |
| *A61K 45/06* | (2006.01) | |
| *A61K 39/00* | (2006.01) | |

(52) U.S. Cl.
CPC .............. *A61K 39/12* (2013.01); *A61K 45/06* (2013.01); *A61K 2039/545* (2013.01); *C12N 2770/24134* (2013.01); *A61K 2039/5254* (2013.01)
USPC ............................ 435/5; 424/218.1; 424/202.1

(58) Field of Classification Search
CPC .................. A61K 39/12; C12N 2770/24011; C12N 2770/24111; C12N 2770/24034; C12N 2770/24134; C12N 2770/24071; C12N 2770/24171
See application file for complete search history.

(56) References Cited

U.S. PATENT DOCUMENTS

| | | | |
|---|---|---|---|
| 7,641,908 B2 * | 1/2010 | Kinney et al. | 424/218.1 |
| 7,718,358 B2 * | 5/2010 | Guy et al. | 435/5 |
| 2004/0120964 A1 | 6/2004 | Mikszta et al. | |
| 2004/0259224 A1 | 12/2004 | Guirakhoo | |
| 2006/0246081 A1* | 11/2006 | Deem et al. | 424/184.1 |
| 2007/0269458 A1 | 11/2007 | Guirakhoo et al. | |
| 2008/0085288 A1 | 4/2008 | Guy et al. | |
| 2010/0158938 A1* | 6/2010 | Guirakhoo | 424/199.1 |
| 2012/0093864 A1 | 4/2012 | Deem et al. | |

FOREIGN PATENT DOCUMENTS

WO   WO2010141386 A1   12/2010

OTHER PUBLICATIONS

Halstead et al., The American Journal of Tropical Medicine and Hygiene, 1973, 22(3):375-381.*
Blaney, Joseph E. Jr. et al., Recombinant, Live-Attenuated Tetravalent Dengue Virus Vaccine Formulations Induce a Balanced, Broad, and Protective Neutralizing Antibody Response against Each of the Four Serotypes in Rhesus Monkeys, Journal of Virology, vol. 79, No. 9, (May 2005) pp. 5516-5528.
Brewoo, Joseph N. et al., Immunogenicity and efficacy of chimeric dengue vaccine (DENVax) formulations in interferon-deficient AG129 mice, ScienceDirect, (Nov. 19, 2011).
Cannon, D.A. et al., Mass vaccination against yellow fever by scarification with 17d strain vaccine, Federal Laboratory Service, Yaba, Lagos, Nigeria, Apr. 30, 1957, pp. 256-263.
Cannon, D.A. et al., Vaccination by scarification with 17d yellow fever vaccine prepared at YABA, Lagos, Nigeria, Laboratory Service Headquarters, Yaba, Lagos, Nigeria, Oct. 8, 1953, pp. 380-393.
Capeding, Rosario Z. et al., Live-attenuated, tetravalent dengue vaccine in children, adolescents and adults in a dengue endemic country: Randomized controlled phase I trial in the Philippines, Elsevier, Vaccine, vol. 29, (2011) pp. 3863-3872.
Dean, Cheryl H. et al., Cutaneous Delivery of a Live, Attenuated Chimeric Flavivirus Vaccine Against Japanese Encephalitis, Human Vaccines, vol. 1, No. 3, (2005) pp. 106-111.
Guy, Bruno et al., Evaluation of Interferences between Dengue Vaccine Serotypes in a Monkey Model, Am.J.Trop.Med.Hyg., vol. 80, No. 2, (2009) pp. 302-311.
Inviragen, Dengue, Feb. 13, 2013, found at http://www.inviragen.com/dengue.php, (2 pages).
Meers, Captain P.D., Further Observations on 17D-Yellow Fever Vaccination by Scarification, With and Without Simultaneous Smallpox Vaccination, Transactions of the Royal Society of Tropical Medicine and Hygiene, vol. 54, No. 5, (1960) pp. 493-501.
Osorio, Jorge E. et al., Development of DENVax: A chimeric dengue-2 PDK-53-based tetravalent vaccine for protection against dengue fever, ScienceDirect, vol. 29, (2011) pp. 7251-7260.
Osorio, Jorge E. et al., Efficacy of a Tetravalent Chimeric Dengue Vaccine (DENVax) in Cynomolgus Macaques, Am.J.Trop.Med. Hyg., vol. 84, No. 6, (2011) pp. 978-987.
Sabin, Albert B., Research on Dengue During World War II, History of Preventive Medicine, U.S. Army Medical Department, World War II, pp. 30-50.
Apt D et al. "Tetravalent neutralizing antibody response against four dengue serotypes by a single chimeric dengue envelope antigen". Vaccine. Jan. 16, 2006; 24(3):335-344, (abstract only).
Huang, Claire et al. "Dengue 2 PDK-53 Virus as Chimeric for Tetravalent Dengue Vaccine Developm,ent" Journal of Virology, p. 11436-11447, Nov. 2003.

(Continued)

*Primary Examiner* — Stacy B Chen
(74) *Attorney, Agent, or Firm* — Faegre Baker Daniels LLP

(57) ABSTRACT

Embodiments of the present invention report compositions and methods for vaccinating a subject against all dengue virus serotypes. In some embodiments, multiple vaccine compositions may be administered to a subject in different anatomical locations in order to induce a rapid response to all dengue virus serotypes. In certain embodiments, administration of two or more vaccine compositions to a subject against all dengue virus serotypes may include two or more routes of administration.

14 Claims, 11 Drawing Sheets

(56) References Cited

OTHER PUBLICATIONS

Webster et al. Lancet Infectious Disease, 2009, 9:678-687.
Zompi and Harris, Viruses, 2012, 4: 62-82.
Higgs et al., "Growth Characteristics of Chimerivax-Den Vaccine Viruses in *Aedes aegypti* and *Aedes albopictus* from Thailand," A J Trop Med Hyg 2006, 75(5):986-993.
International Search Report and Written Opinion, Application No. PCT/US10/36726, Jul. 28, 2010.
Zhou, H. et al., "Sculpting the immunological response to dengue fever by polytopic vaccination", Vaccine, vol. 24, No. 14, Mar. 24, 2006, pp. 2451-2459.
International Search Report and Written Opinion issued in PCT/US2013/045041, dated Dec. 24, 2014, 7 pages.

\* cited by examiner

Pharmajet®

Fig. 3 Immune Response after Primary Immunization
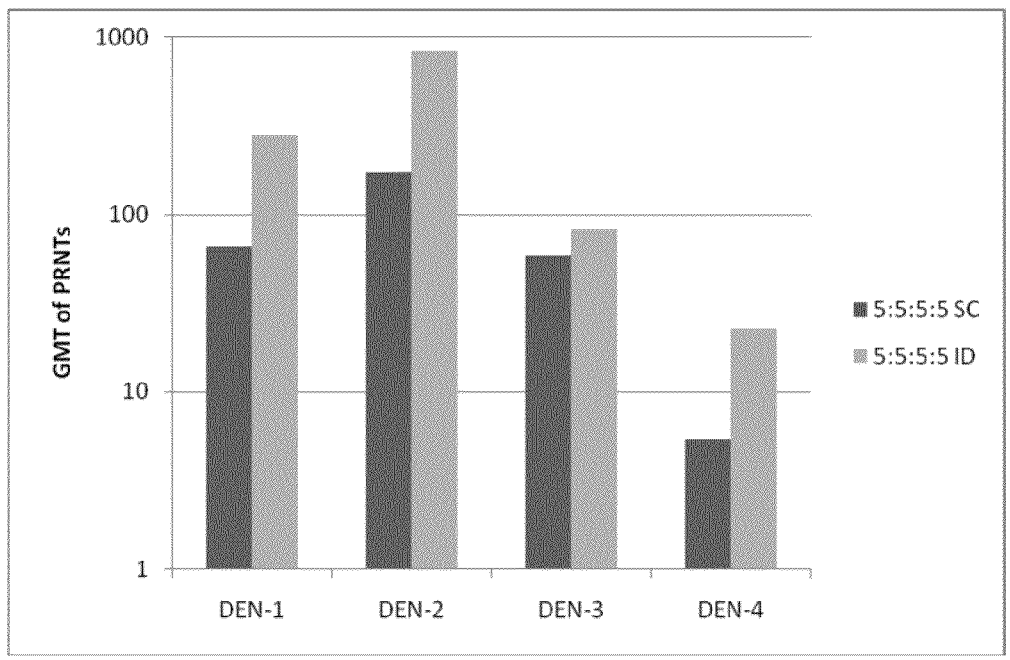
Fig. 4 Immune Response after Boost
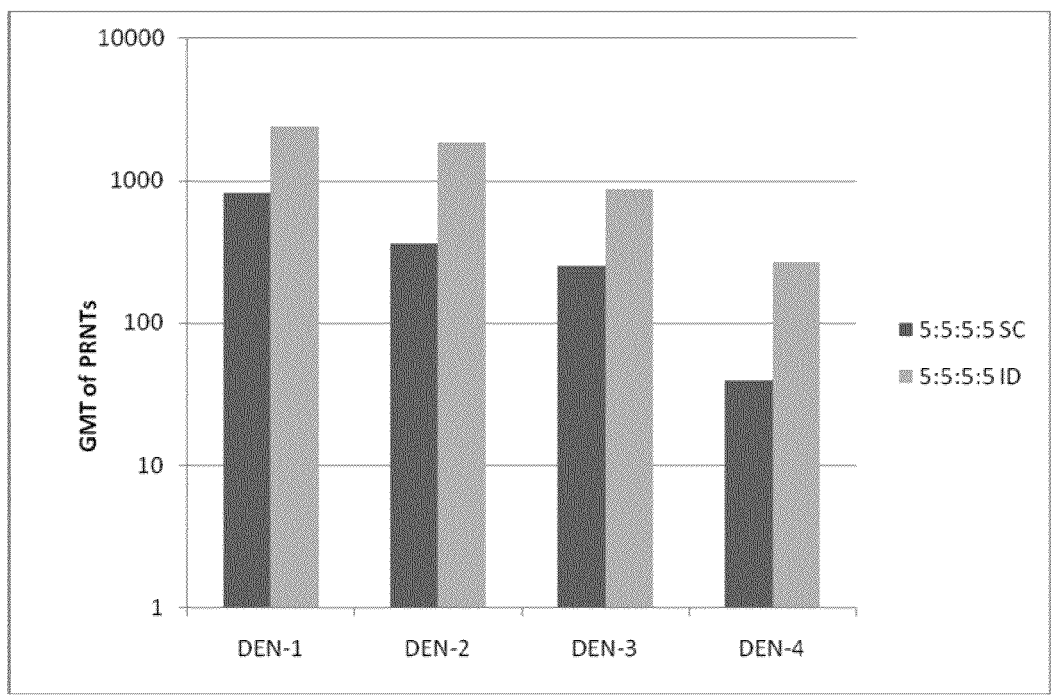

A.

B.

A.

B.

C.

D.

A.

B.

→ DEN-1
→ DEN-2
→ DEN-3
→ DEN-4

A.

B.

C.

D.

COMPOSITIONS AND METHODS FOR RAPID IMMUNIZATION AGAINST DENGUE VIRUS

PRIORITY

This application is a continuation-in-part application and claims the benefit under 35 USC §120 of U.S. Non-Provisional application Ser. No. 12/790,511 filed May 28, 2010 which claims priority under 35 USC §119(e) to U.S. Provisional Application Ser. No. 61/183,020 filed on Jun. 1, 2009. All prior applications are incorporated herein by reference in their entirety for all purposes.

FIELD

Embodiments of the present invention report compositions and methods for administering a vaccine to a subject against all dengue virus strains. In some embodiments, vaccine compositions may be administered by subcutaneous, intradermal, intramuscular or other injection or introduction methods. In certain embodiments, injection in a subject of a vaccine against all dengue virus types includes multiple anatomical sites at day 0. Other embodiments include follow-on injections from within days of the first treatment to up to 12 months after initial injection(s). In other embodiments, no additional injections are needed other than the day 0 treatment. In certain embodiments, subcutaneous, intradermal, intramuscular or other modes of introducing to a subject, a vaccine composition against dengue virus to provide protection against three or more of the dengue serotypes DEN-1, DEN-2, DEN-3 and DEN-4 upon administration at day 0.

BACKGROUND

Vaccines for protection against viral infections have been effectively used to reduce the incidence of human disease. One of the most successful technologies for viral vaccines is to immunize animals or humans with a weakened or attenuated strain of the virus (a "live, attenuated virus"). Due to limited replication after immunization, the attenuated strain does not cause disease. However, the limited viral replication is sufficient to express the full repertoire of viral antigens and can generate potent and long-lasting immune responses to the virus. Thus, upon subsequent exposure to a pathogenic strain of the virus, the immunized individual is protected from disease. These live, attenuated viral vaccines are among the most successful vaccines used in public health.

SUMMARY

Embodiments of the present invention generally relate to methods and compositions for inducing protection in a subject against multiple dengue viruses by, for example, administering a multivalent dengue vaccine to a subject. Some embodiments can include introducing a vaccine composition to a subject via intradermal (ID) injection. In accordance with these embodiments, the vaccine composition can be introduced to a subject intradermally to, for example, to induce neutralizing antibodies against three or more dengue virus serotypes. In certain embodiments, a vaccine composition can include, but is not limited to, a single dose of one formulation of a multivalent dengue serotype vaccine having a predetermined ratio administered to a subject. In other embodiments, a vaccine composition may include, but is not limited to; an initial dose of one formulation of dengue vaccine (e.g. tetravalent formulations such as DENVax™) and then one or more boosts of the same, or a different formulation can be administered to a subject.

Other aspects herein can concern inducing a humoral or cellular immune response in a subject by, for example, introducing a vaccine composition to a subject via an intradermal route wherein the vaccine composition includes, but is not limited to, a dengue virus vaccine. In accordance with these embodiments, compositions disclosed can be administered intradermally to a subject for modulating neutralizing antibody production in the subject against three or more dengue virus serotypes. Some aspects concern predetermined composition ratios (e.g. 1:1:1, 10:1 1:2:2, 1:10; 10:1, 3:4:3:3, 1:4:1; 5:5:4:5; or any ratio of three or more serotypes is contemplated) of the various serotypes of dengue virus or fragments thereof or attenuated compositions thereof in a single vaccine composition in order to increase cross protection and levels of neutralizing antibodies in a subject against at least three dengue virus serotypes when the subject is administered the single vaccine composition.

In certain embodiments, some advantages of using intradermal introduction of a vaccine against dengue virus can include, but are not limited to, multiple protection (cross protection) against some or all dengue virus serotypes in a subject, reduced cost by using reduced volumes of vaccine doses compared to subcutaneous injection, modulation of antibodies produced against some or all dengue virus serotypes in a subject and reduced pain at a site of administration in a subject administered a composition of vaccine against dengue virus.

In some embodiments, a single dose vaccine against dengue virus can include one or more dengue virus serotype(s). In addition, certain embodiments concern treating a subject with at least one additional injection(s) of a vaccine containing multiple dengue viruses administered at a separate site from the first injection, for example, in close proximity to the initial injection or in a distant anatomical site on the subject. In addition, at least one additional intradermal injection(s) may be performed less than 30 days after the first administration to the subject while others are performed 30 days and up to 12 months after the first administration of the vaccine.

Other embodiments disclosed herein relate to methods and compositions for inducing protection in a subject against all dengue virus serotypes by, for example, administering a vaccine to a subject against all dengue virus serotypes in two or more doses on one or more than one anatomical location consecutively within a short interval of time. Some embodiments can include introducing a vaccine composition to a subject via intradermal (ID), subcutaneous (SC), or intramuscular (IM) injection in one location and consecutively in another anatomical location by ID, SC, IM or by other introduction method at a second different anatomical location. Other embodiments include using any combination of modes of administration for introducing a dengue virus vaccine of all dengue virus serotypes to a subject where administration of the vaccine occurs at two or more anatomical sites or by two or more different routes consecutively on the same day to the subject.

Some embodiments include treating a subject in need of dengue virus tetravalent vaccinations consecutively at two or more anatomical locations. In certain embodiments, a subject may need two consecutive administrations in a single day to induce adequate levels of neutralizing antibodies which will protect against dengue infection. In other embodiments, a subject may be administered dengue virus multivalent vaccinations consecutively at two or more anatomical locations, then the subject can be administered at least a third vaccine within 30 days such as about 7, about 14, about 21 or about 28 days later with a composition comprising dengue virus serotypes which may or may not have all serotypes. In other embodiments, a subject may be administered dengue virus tetravalent vaccinations consecutively at two or more anatomical locations on day 0, then the subject can be administered at least a third vaccine within 30 days such as about 7, about 14, about 21 or about 28 days later with a composition comprising dengue virus serotypes which may or may not have all serotypes. Vaccine compositions of these and other embodiments disclosed herein may include two or more dengue virus serotypes at a predetermined ratio for the subsequent administrations beyond the initial dual vaccination. These subsequent vaccinations may depend on personalized titers of antibodies post dual injection or other criteria such as results of test populations. In certain embodiments, a subsequent vaccination may only include a single dengue serotype (e.g. DEN-4).

In certain embodiments, the composition introduced to the subject comprises vaccines against all dengue virus serotypes, for example tetravalent DENVax™ or another similar formulation. DENVax™ comprises a tetravalent dengue vaccine of predetermined ratio where the vaccine is made up of constructs on an attenuated DEN-2 backbone (see for example, PCT Application Number PCT/US01/05142 filed on Feb. 16, 2001 incorporated herein by reference in its entirety for all purposes). In other compositions, all dengue vaccine virus serotypes are in equal proportions in the composition. In yet other compositions, each dengue vaccine virus serotype may be in a particular ratio to one another such that introduction of the composition induces sufficient levels of neutralizing antibodies which would provide the subject with sufficient protection against infection with three or more dengue viruses (e.g. DEN-1, DEN-2, DEN-3 and/or DEN-4). For example, if a subject, after receiving two or more compositions consecutively at two or more anatomical locations and the subject has lower protection to one or more particular dengue virus serotypes, then a booster for that subject can contain a multiple (more than two) vaccine components or a single vaccine component to improve immune responses to all four dengue viruses in the subject. In accordance with these embodiments, samples from a subject may be analyzed for resistance to dengue infection using standard means known in the art.

In certain embodiments, the vaccine composition can be introduced to a subject by any route in multiple anatomical locations to, for example, protect against three or more dengue serotypes after consecutive administrations. In certain embodiments, a vaccine composition can include, but is not limited to, a single dose of a formulation containing all serotypes of dengue virus (e.g. DENVax™) administered to a subject capable of providing protection against at least three dengue virus serotypes. In other embodiments, a vaccine composition can include attenuated dengue virus serotypes in combination with other anti-pathogenic compositions (e.g. Japanese encephalitis, yellow fever, West Nile, influenza, Chikungunya or other). Compositions contemplated herein can be administered by any method known in the art including, but not limited to, intradermal, subcutaneous, intramuscular, intranasal, inhalation, vaginal, intravenous, ingested, and any other method. Introduction in two or more anatomical sites can include any combination administration including by the same mode in two or more anatomical sites or by two or more different modes that include two or more separate anatomical sites. In accordance with these embodiments, two or more anatomical sites can include different limbs. In other embodiments, vaccinations can be delivered to a subject using any device known in the art including, but not limited to, a needle and syringe, jet injection, microneedle injection, patch delivery (e.g. skin), intradermal delivery devices, inhalation device, intranasal device, slow release microparticles, and any other acceptable vaccine-delivery device.

BRIEF DESCRIPTION OF THE DRAWINGS

The following drawings form part of the present specification and are included to further demonstrate certain embodiments. Some embodiments may be better understood by reference to one or more of these drawings alone or in combination with the detailed description of specific embodiments presented.

FIG. 3 represents a bar graph comparison of neutralizing antibody titer produced against different ratios of dengue virus serotypes after a one (primary) administration via the subcutaneous (SC) versus intradermal (ID) route of injection of a vaccine against dengue virus.

FIG. 4 represents a bar graph comparison of neutralizing antibody titer produced against different dengue virus serotypes after a second, boosting administration via the subcutaneous (SC) versus intradermal (ID) injection of a vaccine against dengue virus.

DEFINITIONS

Figure 1:
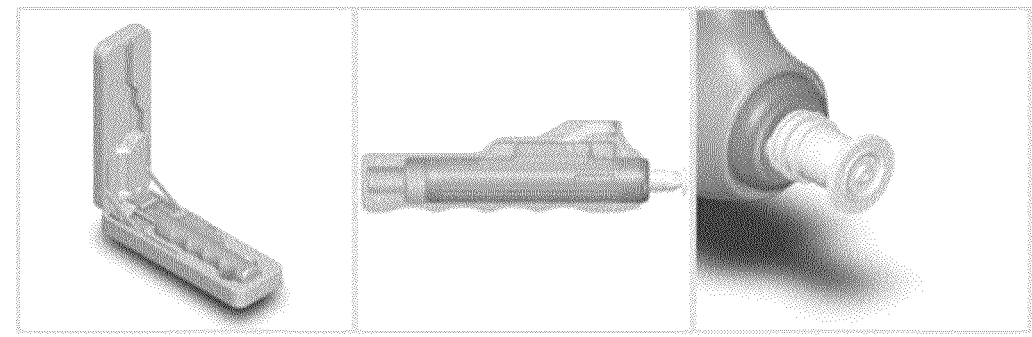
FIG. 1 represents an example of an intradermal injection device currently available.
Figure 2:
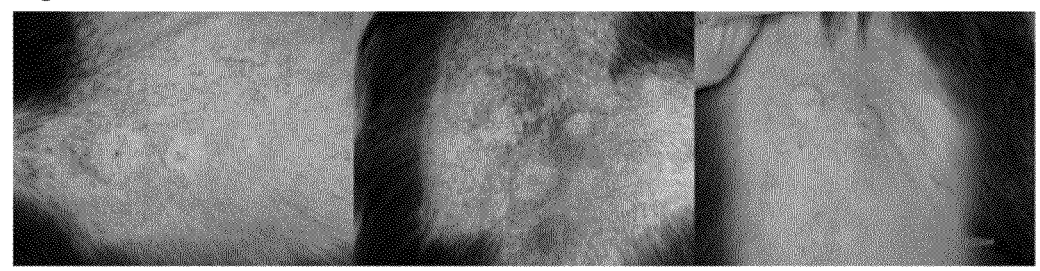
FIG. 2 represents examples of injection sites in a non-human primate subject having intradermal introduction of a vaccine against dengue virus.
Figure 5:
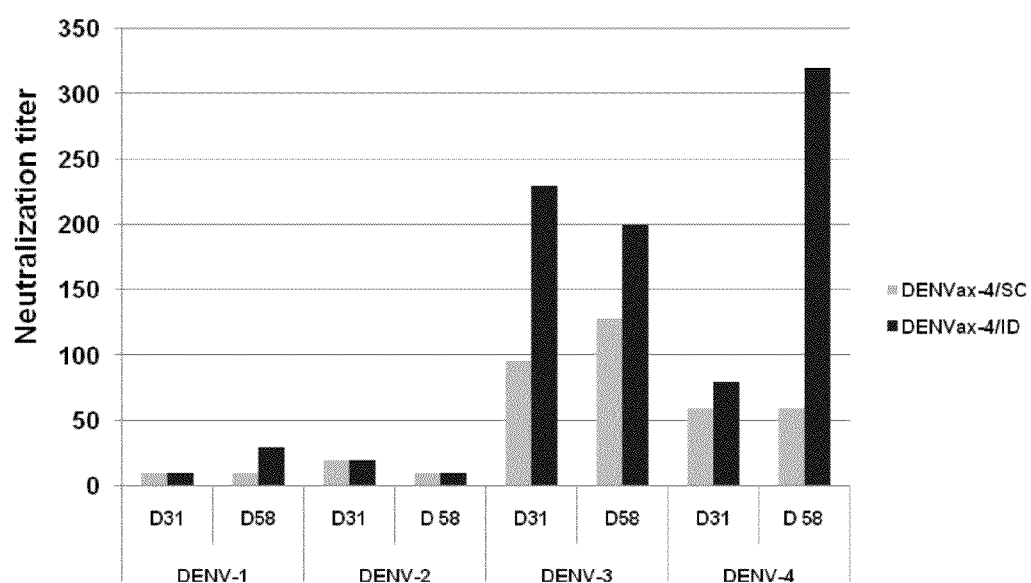
FIG. 5 represents a histogram plot of neutralizing antibody titers after subcutaneous and intradermal immunizations with a vaccine against a dengue virus serotype-4 in mice.
Figure 6A:
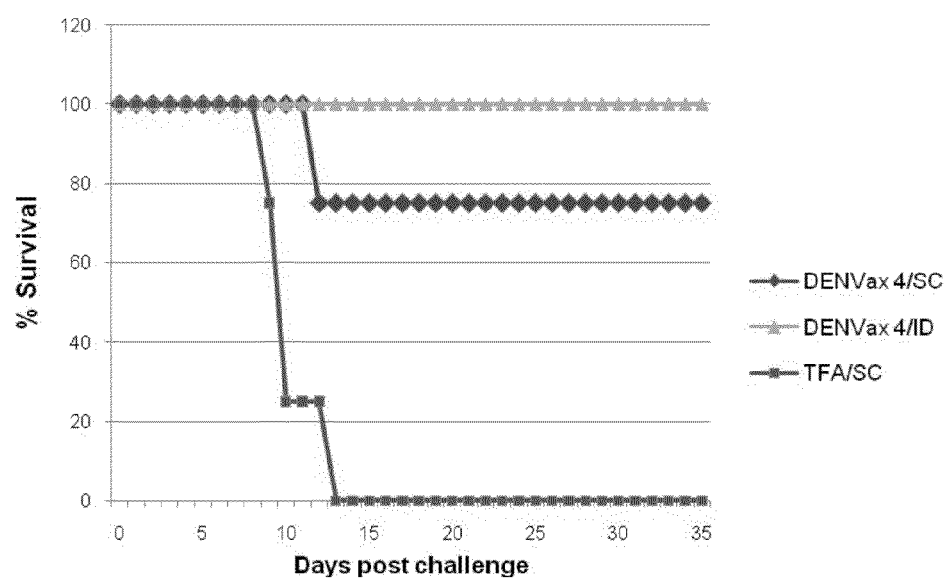
FIGS. 6A and 6B represent graphic depictions of mouse survival after vaccination with a dengue vaccine followed by a challenge with wild-type dengue virus. Mice were vaccinated by SC or ID route of infection with a dengue vaccine (e.g. DENVax-4) or a buffer/placebo (e.g. TFA).
Figure 6B:
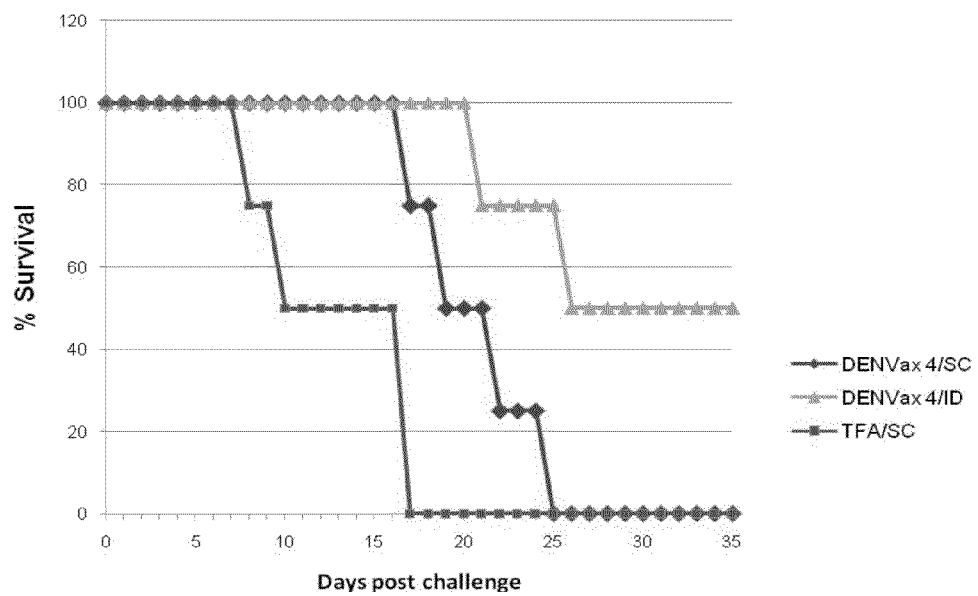
Figure 7:
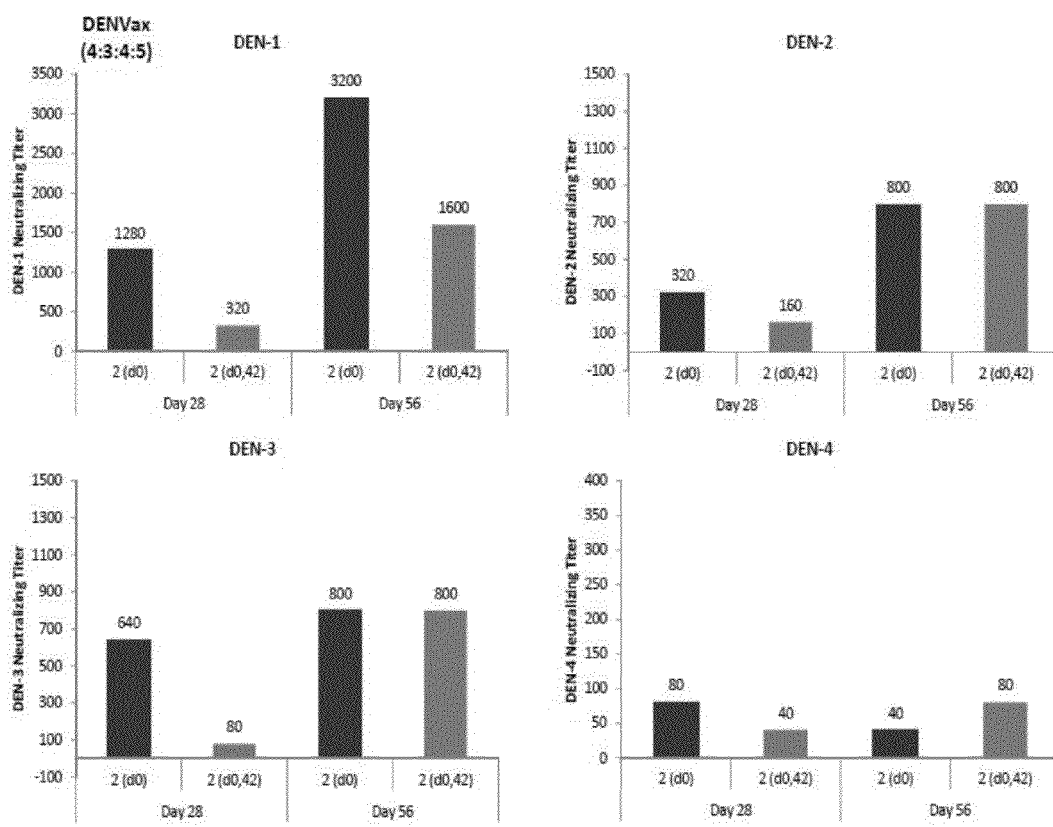
FIG. 7 represents neutralizing antibody titers for DEN-1, DEN-2, DEN-3 and DEN-4 at day 28 and day 56 after two day-0; or 1 day-0 and 1 day-42 injections (e.g. DENVax™; 4:3:4:5 ratio).
Figure 8:
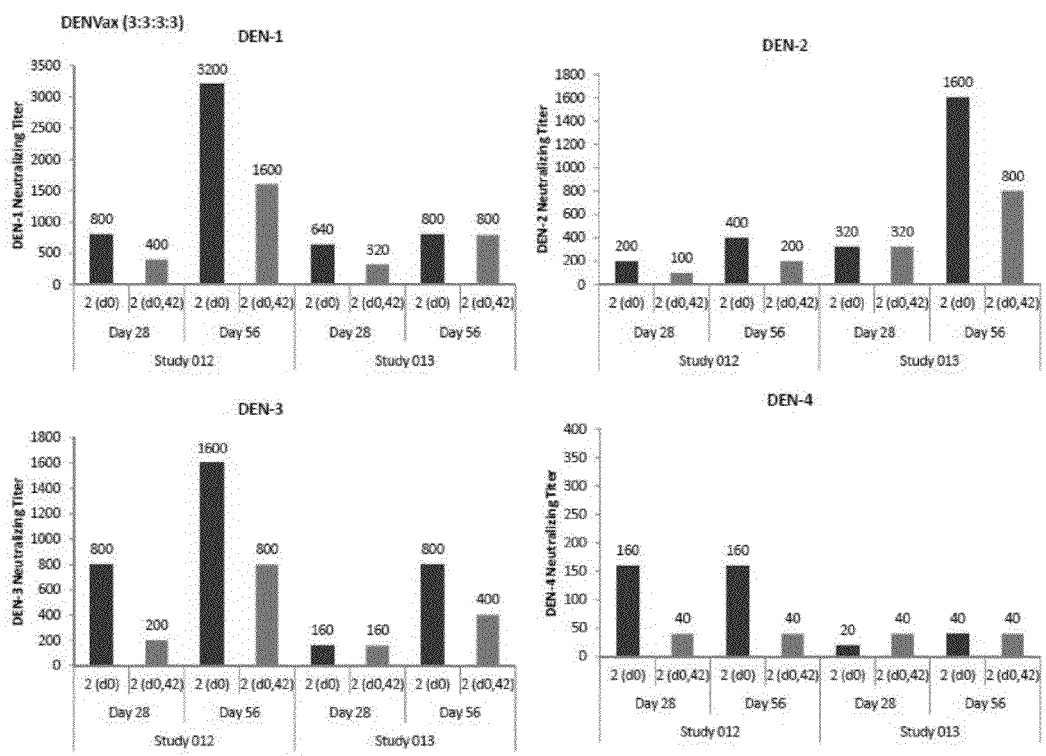
FIG. 8 represents neutralizing antibody titers for DEN-1, DEN-2, DEN-3 and DEN-4 at day 28 and day 56 after two day-0; or 1 day-0 and 1 day-42 injections (e.g. DENVax™; 3:3:3:3, approximately equivalent amounts used).
Figure 9A:
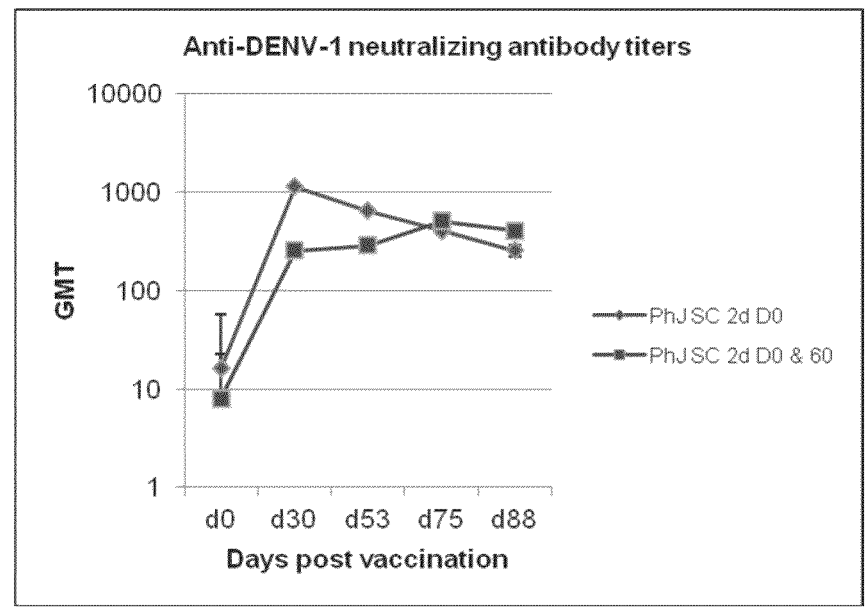
FIGS. 9A-9D represent graphs comparing neutralizing antibody titers achieved in non-human primates after SC immunization with tetravalent dengue virus vaccines. Two groups were vaccinated with the needle-free device via the subcutaneous route either twice on the same day (0,0) or once on day 0 and again on day 60 (0,60).
Figure 9B:
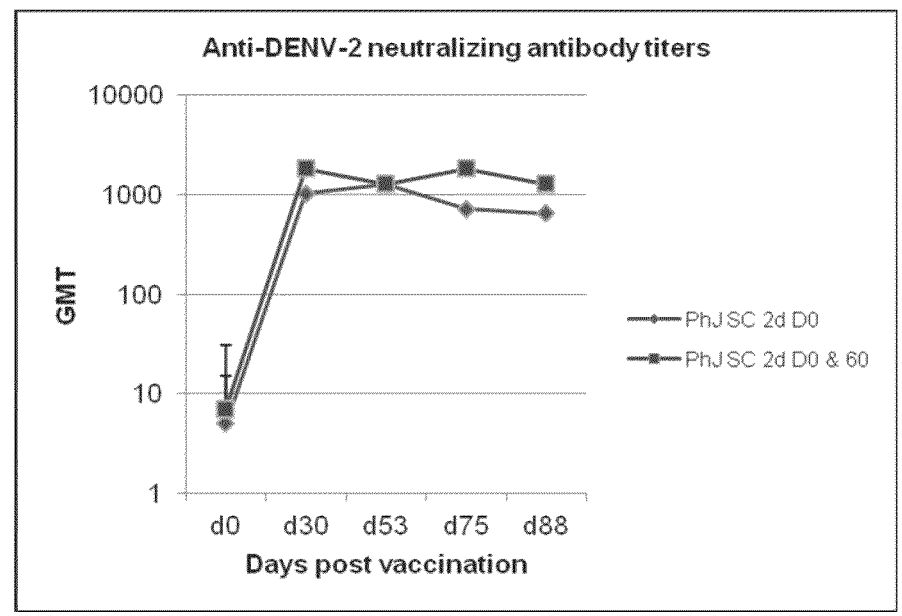
Figure 9C:
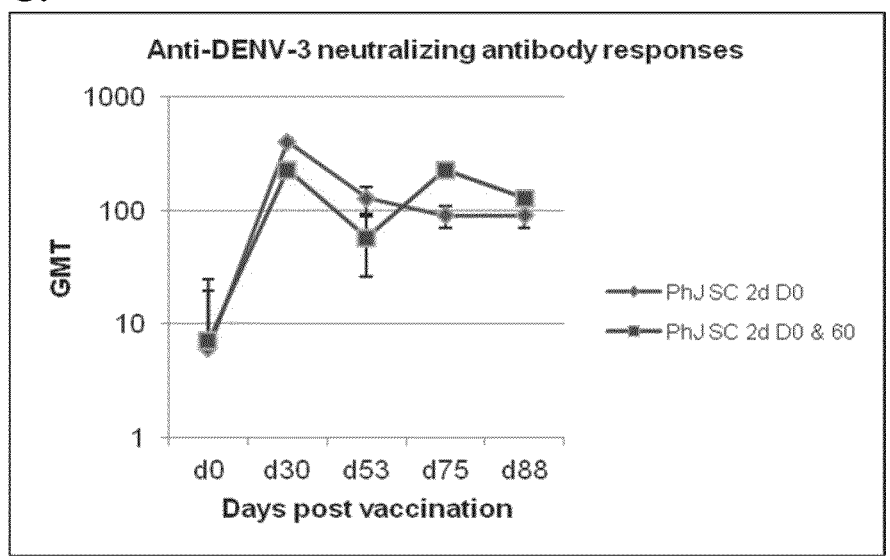
Figure 9D:
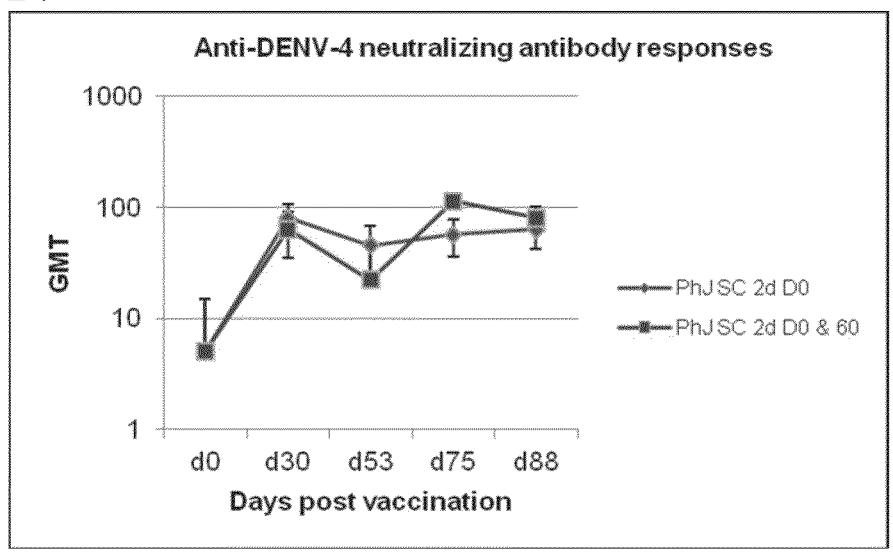

As used herein, "a" or "an" may mean one or more than one of an item.

As used herein, vessel can include, but is not limited to, test tube, mini- or micro-fuge tube, channel, vial, microtiter plate or container.

As used herein the specification, "subject" or "subjects" may include but are not limited mammals such as humans or mammals, domesticated or wild, for example dogs, cats, other household pets (e.g., hamster, guinea pig, mouse, rat), ferrets, rabbits, pigs, horses, cattle, prairie dogs, or zoo animals.

As used herein, "about" or "approximately" can mean plus or minus ten percent.

As used herein, "attenuated virus" can mean a virus that demonstrates reduced or no clinical signs of disease when administered to a subject such as a mammal (e.g., human or an animal).

As used herein, "consecutively" can mean in close temporal proximity, usually within a single patient visit and within 24 hours.

As used herein, "administration" can mean delivery of a vaccine or therapy to an individual animal or human by any one of many methods such as intradermal, subcutaneous, intramuscular, intranasal, inhalation, vaginal, intravenous, oral, buccal, by inhalation, intranasally, or any others known in the art.

DESCRIPTION

In the following sections, various exemplary compositions and methods are described in order to detail various embodiments. It will be obvious to one skilled in the art that practicing the various embodiments does not require the employment of all or even some of the details outlined herein, but rather that concentrations, times and other details may be modified through routine experimentation. In some cases, well-known methods or components have not been included in the description.

Certain aspects of the present invention include, but are not limited to, administration of vaccine compositions against dengue virus.

Embodiments of the present invention generally relate to methods and compositions for inducing protective neutralizing antibodies in a subject against three or more dengue virus serotypes. Other embodiments can include introducing a vaccine composition to a subject via any method known in the art including, but not limited to, intradermal, subcutaneous, intramuscular, intranasal, inhalation, orally, intranasally, vaginal, intravenous, ingested, and any other method wherein the vaccine composition so introduced induces neutralizing antibodies against three or more dengue virus serotypes. In certain embodiments, the vaccine composition comprises a dose of a vaccine against three or more dengue virus serotypes administered to a subject. In other embodiments, the vaccine composition comprises an initial dose against all four dengue serotypes then, one or more other vaccine compositions administered to a subject.

Other aspects of the present invention include modulating an immune response to a vaccine against dengue virus administered intradermally compared to subcutaneously to a subject. Vaccines against dengue virus may include a composition comprising predetermined ratios of all four live, attenuated dengue vaccine viruses, recombinant dengue vaccine viruses, chimeric viruses or mutants thereof. The ratios of various dengue serotypes may be equivalent or nearly equal in representation or certain serotypes may be represented at higher concentrations than others depending on need or ability to induce a balanced neutralizing antibody response in the subject. In accordance with these embodiments, ratios of different dengue vaccines may differ by 2 to 100,000 fold (e.g. plaque forming units) between any two serotypes. This can depend on, for example, number of serotypes represented in the formulation, predetermined response and desired effect. It is contemplated that any dengue vaccine virus serotype formulation may be used to generate a vaccine (e.g. attenuated virus etc.) of use in consecutive administration to a subject in need thereof where the composition includes, but is not limited to, three or more dengue virus serotypes.

In other embodiments, compositions of dengue virus vaccine formulations may be introduced to a subject prior to, during or after exposure to dengue virus by the subject. In accordance with these embodiments, a subject may receive more than one administration consecutively or more than one administration comprising a dengue virus formulation, optionally, followed by one or more additional administrations at a later time. Intradermal, subcutaneous, intramuscular, intranasal, inhalation, vaginal, intravenous, oral, and any other method of applications of formulations described herein may be combined with any other anti-viral treatment. In some embodiments, it is contemplated that intradermal, subcutaneous, intramuscular introduction of a formulation contemplated herein may be administered to any appropriate region of a subject's body (e.g. arm, shoulder, hip, intranasally etc). In addition, parenteral administration of vaccine formulations may be combined with other modes of administration such as intranasal, pulmonary, oral, buccal, or vaginal in consecutive administrations. In some embodiments, it is contemplated that, after consecutive administrations as described herein primary or booster administrations may occur consecutively on the same day, consecutive days, weekly, monthly, bi-monthly or other appropriate treatment regimen.

Dengue is endemic in Asia, Central and South America including Colombia, the Caribbean, the Pacific Islands, and parts of Africa and Australia. It is estimated that 3.6 billion people (55% of the world's population) live in areas at risk of dengue virus transmission (DVI). Infection with a dengue virus can result in a range of symptoms, from subclinical disease to debilitating but transient dengue fever to life-threatening dengue hemorrhagic fever (DHF) or dengue shock syndrome (DSS). Currently, there is no therapeutic treatment or prophylactic vaccine for dengue fever. Given the impact of dengue on populations in endemic countries and on travelers to those regions, a vaccine to prevent dengue is needed.

Dengue is a mosquito borne viral disease, transmitted from human to human primarily by the mosquito, *Aedes aegypti*. Dengue viruses (DEN) contain a single-stranded, positive-sense RNA genome of approximately 11 kb. The genome consists of three structural proteins, capsid (C), premembrane (prM), and envelope (E), and seven nonstructural proteins, NS1, NS2A, NS2B, NS3, NS4A, NS4B, and NS5. There are four different serotypes of dengue viruses, DEN-1, DEN-2, DEN-3 and DEN-4. Primary infection with a given serotype induces lifelong serotype specific immunity. However, there is no long-term cross-protective immunity against the other three dengue virus serotypes, and subsequent infection with an alternate serotype leads to increased probability of more severe disease, such as DHF or DSS.

Due to the disease enhancement associated with secondary DENV infections, a multivalent (e.g. tetravalent) vaccine that stimulates immunity against more than one and up to all four serotypes of DENV is needed. Several DENV vaccine candidates attenuated by classical serial passage in cell culture have proven unsafe or poorly immunogenic. Chimeric live-attenuated, recombinant DENV vaccines candidates, including viruses based on the attenuated genetic background of yellow fever 17D (YF-17D) vaccine virus, DENV-2 PDK-53 vaccine virus, or DENV-4 containing a 30-nucleotide 3' non-coding region (NCR) deletion are known in the art.

A challenging issue in the development of an effective live-attenuated dengue virus (DENV) vaccine is the interference between the four dengue vaccine viruses when administered as a tetravalent formulation. Interference is manifest when one or more components of a multivalent mixture will induce lower immune responses than those elicited by each individual monovalent vaccine. Interference has been observed with vaccines for diseases with multiple pathogenic serotypes, such as polio, dengue or others. Due in part to this interference, it was previously discovered that three dose regimen of oral polio vaccine is required to induce adequate immune responses to the three key serotypes. Historically studies with live attenuated tetravalent dengue vaccines have shown that the DENY serotype that elicits the strongest neutralizing antibody response when administered alone tends to dominate immune responses when administered in the context of a multivalent formulation containing other serotypes. As an example, tetravalent mixtures of four different live, attenuated dengue vaccines showed dominant responses to the DEN-3 component and reduced immune responses to DEN-1, -2 and -4 (see for example, Sabcharoen, et al., 2002, Kitchener, et al. 2006). As a result of this dominance, clinical development of the tetravalent mixtures was suspended. Interference has been seen with recombinant, live attenuated viruses as well. Interference was documented in tetravalent mixtures of dengue/yellow fever chimeras (Guy, et al. 2009. Evaluation of Interferences between Dengue Vaccine Serotypes in a Monkey Model. Am. J. Trop Med. Hyg. 80: 3012-311). In these studies, two serotypes were found to dominate the responses in tetravalent formulations of ChimeriVax vaccine strains. Interference could be overcome by administering two bivalent vaccine formulations, either in separate anatomical locations or sequentially in time, or by a third administration of the tetravalent formulation after one year. Similarly, it was demonstrated that improved multivalent responses with tetravalent recombinant vaccine strains (in this case, formulations containing DENV or chimeric DENV with deletions in the 3' non-coding region) could be obtained only with a prolonged four month internal between the first and second administration. (Blaney, et al., 2005. Recombinant, Live-Attenuated Tetravalent Dengue Virus Vaccine Formulations Induce a Balanced, Broad, and Protective Neutralizing Antibody Response against Each of the Four Serotypes in Rhesus Monkeys. J. Virology 79: 5516-5528).

Successful vaccination often requires vaccine delivery to closely mimic natural infection. To date, all clinical trials of dengue candidate vaccines have utilized the SC route using needle and syringe. The natural route of dengue infection is through mosquito transmission in the dermis. The skin is thought to be an immuno-competent organ functioning as an immune barrier to infections A highly dense network of specialized antigen-presenting cells (APCs, such as Langerhan's cells and dendritic cells) are present in the epidermis and serve to protect the host against infectious pathogens through efficient uptake and presentation of antigens to the regional lymph nodes. Both these subsets of APCs together with resident macrophages have been shown to be natural targets of dengue virus infection. Given the fact that the epidermis is rich in immunocompetent cells, it was contemplated herein that the use of intradermal route for dengue virus vaccine delivery will favor the induction of more potent and balanced immune responses to all four dengue virus serotypes. Specifically, the presence of an increased number of natural host cells in the skin for virus replication may reduce interference and permit replication of the less dominant viruses in tetravalent formulations. In certain embodiments, intradermal immunization of multivalent, live, attenuated dengue vaccines can be used to induce more balanced immune responses to dengue virus exposure in a subject.

Certain embodiments disclosed herein concern DENVax™. DENVax™ is a dengue vaccine that consists of a mixture of four recombinant dengue virus strains designed to generate immune responses to the four dengue serotypes (DEN-1, DEN-2, DEN-3 and DEN-4). Not to be bound by any limitations to a particular tetravalent formulation, DENVax™, the dengue serotype 2 vaccine component (DENVax-2) corresponds to an attenuated DEN-2 PDK-53 strain. This construct has already been investigated in many clinical studies. The other dengue vaccine strains (DENVax-1, DENVax-3 and DENVax-4) are chimeras consisting of the DEN-1, DEN-3 or DEN-4 structural pre-membrane (prM) and envelope (E) protein genes cloned into a DEN-2 PDK-53 non-structural gene backbone. These recombinant viruses express the surface antigens of DEN-1, DEN-3 or DEN-4 and retain the genetic alterations responsible for the attenuation of the DEN-2 PDK-53 strain. In certain embodiments, DENVax™ can be used as an example of a multivalent live, attenuated dengue vaccine having all four dengue virus serotypes represented in one vaccine composition at various ratios. Other embodiments relate to optimizing tetravalent vaccine administrations. Yet other embodiments relate to DENVax™ immunization methods.

During the course of exploring intradermal delivery of multivalent dengue vaccines, it was discovered that administration of more than one dose of a multivalent vaccine in at least two separate anatomical sites induced neutralizing antibody responses that were approximately equivalent or superior to administering multiple doses separated by time. Further, it was discovered that the benefit of multiple site administration was independent of the route of immunization.

This finding was unexpected. Information was previously disclosed regarding multiple subcutaneous administrations of a tetravalent vaccine based on deleted, attenuated and/or recombinant viruses. It was reported that a second administration of a tetravalent administration 30 days after the first administration failed to increase neutralizing antibody titers. In contrast, a second administration 120 days after the first, improved neutralizing antibody titers to all four dengue serotypes. Similar information was reported in clinical trials of yellow fever/dengue recombinant vaccines (Poo, et al. 2011 Ped. Inf. Dis J. 30: 1-9) It was also suggested that a three month interval between administrations was suboptimal for generating neutralizing antibody response against multiple dengue viruses. (Capeding et al. 2011 Vaccine 29: 3863-3872) These reports regarding two clinical studies suggested that longer intervals such as 6-9 months are required to generate better multivalent immune responses. Lastly, in early human challenge studies, it was reported that wild type dengue viruses elicit broadly cross-reactive antibodies that persist for up to 6 months after initial infection. These data support the concept that a short immunization regimen are suboptimal for live attenuated vaccines: the transient cross-reactive antibodies previously observed would effectively neutralize any of the live, attenuated vaccine components in a multivalent formulation. Until the instant disclosure, immunization regimens with multivalent, live attenuated vaccines at shorter intervals in more than one anatomical site were not considered a viable option for treating a subject in need of such a treatment. It is contemplated herein that multiple site administration, by accessing larger numbers of antigen presenting cells and/or more than one draining lymph node, permits immune responses to less dominant components of a multivalent, live attenuated vaccine and effectively reduces vaccine interference.

In certain embodiments, the composition introduced to the subject comprises vaccines against all dengue virus serotypes (DEN-1, DEN-2, DEN-3, DEN-4). In other embodiments, a composition contemplated herein can include DENVax™ or other similar formulation. In some compositions, vaccine viruses against all dengue serotypes are in equal proportions in the composition. In yet other compositions, each dengue vaccine virus serotype may be in a particular ratio to one another such that introduction of the composition provides the subject with sufficient levels of neutralizing antibodies against all dengue viruses (e.g. DEN-1, DEN-2, DEN-3, DEN-4).

Certain embodiments disclosed herein relate to methods and compositions for a rapid induction of protection in a subject against all dengue virus serotypes by, for example, administering a vaccine to a subject against all dengue virus serotypes in more than one anatomical location consecutively on the same day. Some embodiments can include introducing a vaccine composition to a subject via intradermal (ID) or subcutaneous (SC) injection or other administration mode in one anatomical location then introducing at least a second vaccine composition at another anatomical location by ID, SC or other administration mode. Some embodiments include using any combination of modes of administration for introducing a dengue virus vaccine of all dengue virus serotypes to a subject where administration of the vaccine occurs at two or more anatomical sites or by two or more different routes on day 0 to the subject. Some embodiments include using the same mode of administration but at different anatomical locations.

Some dengue virus vaccine compositions described herein range in dosage from from $10^2$ to $5\times10^6$ PFU for each serotype in a composition. Other compositions (e.g. follow-on vaccinations) contemplated herein include compositions that have dosages less than or more than this range based on immune response in the subject after primary immunization. In certain embodiments, ratios can vary for the various Dengue vaccine virus serotypes depending on need and immune response in a subject.

In certain embodiments, compositions introduced on the first vaccination or in any follow-on vaccination contemplated herein may include one tetravalent dengue virus composition. In accordance with these embodiments, the composition can include DENVax™ or other similar tetravalent formulation of equal or equivalent ratios or at predetermined serotype ratios. Other embodiments, can include using different formulations (e.g. serotype ratios) for each of the vaccine compositions administered at the primary vaccination or any follow-on vaccinations (e.g. less than 30 days later).

Some embodiments herein include treating a subject in need of such a vaccine, on day 0 at two or more anatomical locations then administering at least a second vaccine within 30 days such as about 7, about 14, about 21 or about 28 days later with a composition comprising dengue virus serotypes which may or may not have all serotypes. In certain embodiments, each vaccination has all dengue virus serotypes represented in the vaccine formulation. Vaccine compositions of follow-on administration disclosed herein may include two or more dengue virus serotypes at a predetermined ratio for the subsequent administration(s).

In certain embodiments, the composition introduced to the subject comprises all dengue virus serotypes. In some embodiments, vaccine compositions comprise various formulations of DENVax™ or other similar formulation. In certain vaccine compositions, the ratio of DEN-1:DEN-2:DEN-3:DEN-4 can be 3:3:3:3, 4:3:4:5, 5:4:5:5, 5:4:5:5, 5:5:5:5, 10:1:10:100 or other ratio where the ratio between 2 serotypes can be about 2 to about 100,000 fold difference (e.g. $DENVax_{4:3:4:5}$™ etc.) in a single composition. In certain embodiments a dengue serotype ratio can be DEN-1 at $2\times10^4$: DEN-2 at $5\times10^4$: DEN-3 at $1\times10^5$: DEN-4 at $3\times10^5$ PFUs or DEN-1 at $8\times10^3$: DEN-2 at $5\times10^3$: DEN-3 at $1\times10^4$: DEN-4 at $2\times10^5$ PFUs. In some compositions, all dengue vaccine virus serotypes are in equal proportions in the composition. In yet other compositions, each dengue vaccine virus serotype may be in a particular ratio to another serotype such that introduction of the composition provides the subject with adequate or more than adequate levels of neutralizing antibodies which confer protection against all dengue viruses (e.g. Dengue 1, 2, 3 and 4). For example, if after receiving two or more consecutive vaccinations on day 0 at two or more anatomical locations, the subject has lower protection to one or more particular dengue virus serotypes, then a booster for that subject can contain an increased concentration of the one or more dengue vaccine virus serotype (that demonstrated lower neutralizing antibodies) to provide better protection against all dengue virus types. In accordance with these embodiments, samples from a subject may be analyzed for an immune response to dengue serotype infection (e.g. Dengue-1, -2, -3, -4) using standard means known in the art.

In certain embodiments, the vaccine composition can be simultaneously or consecutively introduced to a subject intradermally in multiple anatomical locations to, for example, protect against all dengue serotypes (e.g. cross protection). In certain embodiments, a vaccine composition can include, but is not limited to, a single formulation of all dengue vaccine virus serotypes (e.g. DENVax™) administered to a subject capable of providing full protection against infection by all dengue virus serotypes. In other embodiments, a vaccine composition can include attenuated dengue virus serotypes in combination with other anti-pathogenic compositions (e.g. Japanese encephalitis, West Nile, influenza etc.). Compositions contemplated herein can be administered by any method known in the art including, but not limited to, intradermal, subcutaneous, intramuscular, intranasal, inhalation, vaginal, intravenous, ingested, and any other method. Introduction in two or more anatomical sites can include any combination administration including by the same mode in two or more anatomical sites or by two different modes that include two separate anatomical sites. In accordance with these embodiments, two or more anatomical sites can include different limbs.

For example, if a subject, after receiving two or more consecutive vaccinations on day 0 at two or more anatomical locations and the subject does not induce poor levels of neutralizing antibodies to one or more particular dengue virus serotypes, then a booster vaccination for that subject can contain an increased concentration of the one or more dengue vaccine virus serotype (that demonstrated lower levels of neutralizing antibodies) to provide complete protection against infection by all dengue virus types. In accordance with these embodiments, samples from a subject may be analyzed for resistance to dengue infection using standard means known in the art.

In certain embodiments, two doses of the vaccine composition can be consecutively introduced to a subject in multiple anatomical locations to, for example, to protect against all dengue serotypes (e.g. cross protection) at day 0. In certain embodiments, a vaccine composition can include, but is not limited to, a single dose of dengue vaccine viruses for all serotypes (e.g. DENVax™) administered to a subject capable of inducing neutralizing antibodies to levels which would provide full protection against infection by all dengue virus serotypes. Thus, a particular subject may need to visit a clinic only one time to receive enough protection to visit or remain in a region having dengue virus for a predetermined period of time (e.g. 30 days). In other embodiments, a vaccine composition can include attenuated dengue virus serotypes in combination with vaccine compositions against other pathogens (e.g. flaviviruses such as Japanese encephalitis, West Nile, or other viruses such as influenza etc.). Compositions contemplated herein can be administered by any method known in the art including, but not limited to, intradermal, subcutaneous, intramuscular, intranasal, inhalation, vaginal, intravenous, ingested, and any other method. Introduction in two or more anatomical sites can include any combination administration including by the same mode in two or more anatomical sites or by two or more different modes that include two or more separate anatomical sites. In accordance with these embodiments, two or more anatomical sites can include different limbs, different tissues, intranasally, as drops (e.g. for the eye), intramuscular in two or more locations.

In certain embodiments, vaccine compositions disclosed herein can be chimeric constructs that can include a mixture of constructs that make up at least 3 dengue serotypes in a vaccine composition for administration to a subject. In other embodiments, dengue virus vaccines can include constructs having an attenuated flavivirus backbone with various dengue serotype substitutions representing each of the four serotypes where the constructs can be mixed in a composition for administration as a vaccine.

Tetravalent formulations, e.g. DENVax™, can be prepared by mixing predetermined amounts of each monovalent vaccine component. Based on input titer of each vaccine component, a defined volume of monovalent vaccines can be added to a final volume of either 0.1 mL (e.g. for intradermal) or 0.5 mL (e.g. for subcutaneous) vaccine formulation. The remaining volume of the tetravalent DENVax™ vaccine can be composed of diluent containing Trehalose (15%) F127 (1%) and human serum albumin (0.1%) in a saline buffer to stabilize the live, attenuated vaccine formulation.

Methods

Nucleic Acid Amplification

Nucleic acids may be used in any formulation or used to generate any formulation contemplated herein. Nucleic acid sequences used as a template for amplification can be isolated viruses (e.g. dengue viruses), according to standard methodologies. A nucleic acid sequence may be genomic DNA or fractionated or whole cell RNA. Where RNA is used, it may be desired to convert the RNA to a complementary cDNA. In some embodiments, the RNA is whole cell RNA and is used directly as the template for amplification. Any method known in the art for amplifying nucleic acid molecules is contemplated (e.g., PCR, LCR, Qbeta Replicase, etc).

Expressed Proteins or Peptides

Genes can be expressed in any number of different recombinant DNA expression systems to generate large amounts of the polypeptide product, which can then be purified and used in methods and compositions reported herein. Any method known in the art for generating and using constructs is contemplated. In certain embodiments, genes or gene fragments encoding one or more polypeptide may be inserted into an expression vector by standard cloning or subcloning techniques known in the art.

Proteins, peptides and/or antibodies or fragments thereof may be detected or analyzed by any means known in the art. In certain embodiments, methods for separating and analyzing molecules may be used such as gel electrophoresis or column chromatography methods.

Electrophoresis

Electrophoresis may be used to separate molecules (e.g., large molecules such as proteins or nucleic acids) based on their size and electrical charge. There are many variations of electrophoresis known in the art. A solution through which the molecules move may be free, usually in capillary tubes or it may be embedded in a matrix or other material known in the art. Common matrices can include, but are not limited to, polyacrylamide gels, agarose gels, mass spec, blotting and filter paper.

Some embodiments, using a gene or gene fragment encoding a polypeptide may be inserted into an expression vector by standard subcloning techniques. An expression vector may be used which produces the recombinant polypeptide as a fusion protein, allowing rapid affinity purification of a peptide or protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6×His system (Qiagen, Chatsworth, Calif.).

Pharmaceutical Formulations

Any pharmaceutical formulation known in the art for a vaccine is contemplated herein. In certain embodiments, a formulation can contain one or more dengue virus serotype in various ratios in a single vaccine. It is contemplated that formulations can contain other agents of use in vaccination of a subject including, but not limited to other active or inactive ingredients or compositions known to one skilled in the art.

All contemplated vaccinal viruses herein can be administered in the form of vaccinal compositions which can be prepared by any method known to one skilled in the art. In certain embodiments, the virus compositions are lyophilized and are mixed with a pharmaceutically acceptable excipient (e.g. water, phosphate buffered saline (PBS), wetting agents etc.) In other embodiments, vaccine compositions can include stabilizers that are known to reduce degradation of the formulation and prolong shelf-life of the compositions.

In other embodiments, an adjuvant may be added to the composition to induce, increase, stimulate or strengthen a cellular or humoral immune response to administration of a vaccination described herein. Any adjuvant known in the art that is compatible with compositions disclosed herein is contemplated.

Some embodiments herein concern amounts or doses or volumes of administration of a tetravalent dengue virus composition and the amount or dose can depend on route of administration and other specifications such as the subject getting the vaccine (e.g. age, health condition, weight etc.).

It is contemplated herein that compositions described can be administered to a subject living in an area having dengue virus, a subject traveling to an area having dengue virus or other subject such as any human or animal capable of getting dengue fever or other dengue virus condition. In certain embodiments, it may be recommended that a subject traveling to an area having dengue virus is administered one or more vaccine compositions (e.g. two or more on Day 0) about 1 to about 3 months prior to dengue virus exposure. Vaccines herein can be administered as a prophylactic treatment to prevent infection in adults and children. A subject can be naïve or non-naïve subject with respect to exposure to dengue virus and vaccine regimens disclosed herein.

Kits

Other embodiments concern kits of use with the methods (e.g. methods of application or administration of a vaccine) and compositions described herein. Some embodiments concern kits having vaccine compositions of use to prevent or treat subjects having been exposed or suspected of being exposed to one or more dengue viruses. In certain embodiments, a kit may contain one or more than one formulation of dengue virus serotype(s) (e.g. attenuated vaccines, trivalent or tetravalent formulations, DENVax™) at predetermined ratios. Kits can be portable, for example, able to be transported and used in remote areas such as military installations or remote villages in dengue endemic areas. Other kits may be of use in a health facility to treat a subject having been exposed to one or more dengue viruses or suspected of being at risk of exposure to dengue virus.

Kits can also include a suitable container, for example, a vessel, vials, tubes, mini- or microfuge tubes, test tube, flask, bottle, syringe or other container. Where an additional component or agent is provided, the kit can contain one or more additional containers into which this agent or component may be placed. Kits herein will also typically include a means for containing the agent (e.g. a vessel), composition and any other reagent containers in close confinement for commercial sale. Such containers may include injection or blow-molded plastic containers into which the desired vials are retained. Optionally, one or more additional agents such as immunogenic agents or other anti-viral agents, anti-fungal or antibacterial agents may be needed for compositions described, for example, for compositions of use as a vaccine against one or more additional microorganisms.

In other embodiments, kits can include devices for administering one or more vaccination to a subject such as an ID, SQ, IM, an inhaler, intranasal applicator or other device for administering a vaccine composition disclosed herein.

The following examples are included to demonstrate certain embodiments presented herein. It should be appreciated by those of skill in the art that the techniques disclosed in the examples that follow represent techniques discovered to function well in the practices disclosed herein. However, those of skill in the art should, in light of the present disclosure, appreciate that many changes can be made in the certain embodiments which are disclosed and still obtain a like or similar result without departing from the spirit and scope herein.

EXAMPLES

Example 1

Previous studies revealed that natural infection with each DENV (dengue virus) serotype leads to long-lived protection against dengue fever caused by the homologous serotype. In certain embodiments, administration of an effective dengue vaccine closely mimics natural infection and can serve as a mode for administering vaccines against Dengue virus. Embodiments reported herein can concern a natural infection route of dengue virus (DENV) infection, similar to intradermal delivery by the transporting host, a mosquito bite. In certain embodiments, intradermal injection to deposit the vaccine viruses into the same tissue can be used. Skin is a highly accessible organ and represents an effective immune barrier, mainly attributed to the presence of Langerhans cells (LCs) residing in the epidermis. Skin immunization elicits a broad range of immune responses, including humoral, cellular, and mucosal and has the potential to bypass the effect of pre-existing immunity on the immunogenicity of administered vaccines.

Some embodiments for intradermal (ID) administration of the tetravalent dengue vaccines in a subject in need of such a treatment are reported. One exemplary method of intradermal administration was performed on four Cynomologous macaques administered a DENVax™ ((DENVax-1: $1\times10^5$ PFU, DENVax-2; $1\times10^5$ PFU, DENVax3: $1\times10^5$ PFU, DENVax4: $1\times10^5$ PFU) Dengue virus vaccine) by intradermal administration. To achieve an equivalent dose of virus, 0.15 ml of vaccine was deposited ID in three closely spaced sites using a needle-free jet injector (see FIGS. 1 and 2, below). FIG. 1 represents an intradermal inject (e.g., PharmaJet® or other intradermal device) device used for intradermal inoculations.

FIG. 2 illustrates inoculation sites on Cynomolgus macaques post vaccination with PharmaJet device. Animals were boosted 60 days later with the same formulation by the same route. Serum samples were collected at predetermined intervals, days 15, 30, 58, 74, and 91 and were tested for the presence of neutralizing antibodies directed against the four Dengue serotypes. PRNT (plaque reduction neutralization test, known in the art for quantifying levels of anti-DEN neutralizing antibodies) were performed on the sera samples.

It was demonstrated that the neutralizing antibody titers are significantly higher after ID administration as compared to SC administration ($p<0.05$ for DENV-1 and DENV-2) after a primary administration (see FIG. 3) or after a secondary administration ($p<0.05$ for all DENV serotypes) (See FIG. 4). Since the sites were closely spaced in the same area, and each innoculum consists of all four viruses, this mode of vaccine delivery closely resembles a single administration of DENVax™. FIG. 3 illustrates 50% PRNT (plaque reduction neutralization titers) Geometric Mean Titers at Day 58 (58 days after the primary administration). FIG. 4 illustrates 50% PRNT Geometric Mean Titers at Day 74 (14 days after the secondary administration on Day 60). As can be seen in the figures, the neutralizing antibody titers to all four dengue viruses were higher after intradermal versus subcutaneous administration. In addition, the number of animals that demonstrated neutralizing antibody responses ("seroconversion" defined as PRNT >10) was greater after the first dose of vaccine (see Table 1, the percentage of animals that seroconverted to each of the four Dengue serotypes is shown after primary and secondary immunization).

TABLE 1

Seroconversion of non-human primates after dengue immunization

| DENVax Formulation | % Seroconversion | | | | | | | |
|---|---|---|---|---|---|---|---|---|
| | DEN-1 | | DEN-2 | | DEN-3 | | DEN-4 | |
| | Prime | Boost | Prime | Boost | Prime | Boost | Prime | Boost |
| 5:5:5:5 SC | 87.5% | 100.0% | 100.0% | 100.0% | 75.0% | 100.0% | 50.0% | 100.0% |
| 5:5:5:5 ID | 100.0% | 100.0% | 100.0% | 100.0% | 100.0% | 100.0% | 100.0% | 100.0% |

The immunized animals were tested for protection against challenge with wild type dengue viruses. In cynomolgus macaques, wild type dengue virus infection leads to virus replication and viremia, but no clinical signs. At day 91, two monkeys were challenged with DENV-1 (Dengue virus serotype 1) and two monkeys challenged with DEN-2 (Dengue virus serotype 2). Serum samples were collected daily for 11 days after challenge. Levels of dengue virus RNA were measured in the samples by quantitative real-time polymerase chain reaction technology (q-rtPCR) and titers of viable virus were measured by virus isolation and plaque formation on Vero cells. The results are shown in Tables 2 and 3. Neutralizing antibodies against DEN-1 at Day 91, just prior to challenge ("Pre-Challenge") and Day 105, 14 days after challenge ("Post"). Viremia is given as the number of days that live DEN-1 virus could be isolated from blood samples ("Duration") and the log 10 of the peak titer isolated from each animal. Viral RNA is given as the number of days viral RNA could be detected in the serum samples ("Duration") and peak viral RNA levels in each monkey, expressed as the log 10 of the number of viral RNA genomes detected.

After challenge, the SC and ID immunized animals were completely protected from DEN-1 or DEN-2 induced viremia (compared to the control animals that demonstrated significant viremia of long duration). In all of the ID immunized animals, but not all of the SC immunized animals, there was also an absence of viral RNA replication and a lack of an increase in antibody titer after challenge (compare the ID animals to SC injected CY0181, CY0172 or the control animals). These data suggest that protection is "sterilizing" and prevents any virus replication after challenge.

Example 2

In another example, an optimized DENVax™ formulation delivered in different locations and with different timings will be tested in non-human primates. Groups of eight Cynomolgus macaques will be immunized with a DENVax™ formulation containing $1\times10^5$ plaque forming units (pfu), $1\times10^4$ pfu, $1\times10^5$ pfu and $1\times10^5$ pfu of DENVax™-1, DENVax™-2, DENVax™-3 and DENVax™-4, respectively (abbreviated 5:4:5:5). Two doses will be administered in 0.1 ml ID. Groups

TABLE 2

Responses after challenge with DEN-1

| Monkey | Formulation | DEN-1 PRNT | | Viremia | | Viral RNA | |
|---|---|---|---|---|---|---|---|
| | | Pre-Challenge | Post | Duration | Peak | Duration | Peak |
| CY0174 | 5:5:5:5 SC | 240 | 240 | 0 | 0 | 0 | 0 |
| CY0181 | 5:5:5:5 SC | 640 | 61440 | 0 | 0 | 5 | 5.6 |
| CY0192 | 5:5:5:5 ID | 1920 | 1280 | 0 | 0 | 0 | 0 |
| CY0194 | 5:5:5:5 ID | 7680 | 1920 | 0 | 0 | 0 | 0 |
| CY0061 | Controls | 1 | 2560 | 6 | 2.0 | 9 | 5.7 |
| CY0193 | Controls | 25 | 2560 | 3 | 2.7 | 7 | 6.4 |
| CY0058 | Controls | 1 | 640 | 5 | 2.9 | 7 | 5.5 |
| CY0073 | Controls | 1 | 1280 | 5 | 3.6 | 10 | 6.2 |

TABLE 3

Responses after challenge with DEN-2

| Monkey | Formulation | DEN-2 PRNT | | Viremia | | Viral RNA | |
|---|---|---|---|---|---|---|---|
| | | Pre-Challenge | Post | Duration | Peak | Duration | Peak |
| CY0172 | 5:5:5:5 SC | 3413 | 3413 | 0 | 0 | 1 | 3.9 |
| CY0177 | 5:5:5:5 SC | 853 | 533 | 0 | 0 | 0 | 0 |
| CY0198 | 5:5:5:5 ID | 240 | 320 | 0 | 0 | 0 | 0 |
| CY0201 | 5:5:5:5 ID | 1920 | 1600 | 0 | 0 | 0 | 0 |
| CY0088 | Controls | 6 | 10240 | 6 | 2.3 | 8 | 5.1 |
| CY0199 | Controls | 1 | 3640 | 5 | 1.8 | 9 | 4.7 |
| CY0065 | Controls | 1 | 10240 | 5 | 2.9 | 8 | 5.8 |
| CY0104 | Controls | 1 | 10240 | 4 | 2.4 | 8 | 5.7 | will be immunized with either one dose in each arm at Day 0, one dose in one arm at Day 0 and one dose in the other arm at Day 7, or one dose in one arm at Day 0 and one dose in the other arm at Day 60. These groups will be compared to a group that receives the same dose (5:4:5:5) in three sites in the same are on Day 0 and three sites in the other arm on Day 60 as well as a group that receives the same dose in a single 0.5 ml SC immunization in one arm at Day 0 and in the other arm at Day 60. A control group will be immunized with vaccine excipients only (no vaccine viruses). Following immunization, blood samples will be collected on days 0, 7 (for peak viremia), 15, 30, 60, and 90 to test the neutralizing antibodies against the four Dengue virus serotypes by PRNT50. PBMCs collected on days 30, 60, 90 will be also monitored for IFN-γ secretion by an ELISPOT assay. On day 90, two animals from each group will be challenged with wild type of DEN-1, DEN-2, DEN-3, or DEN-4 viruses. Challenged animals will be monitored for clinical signs and temperature (twice daily), changes in food consumption (once daily) and body weight (weekly). In addition, all animals will be bled daily for 11 days post-challenge to monitor viremia and hematological parameters. Again, the speed and duration of PRNT responses to all four DEN viruses and protection after day 90 challenge will be assessed. It is believed that intradermal administration in multiple sites and in distinct anatomical locations may be more effective than subcutaneous administration as a single bolus. Multiple sites can provide exposure of the vaccine to more antigen presenting cells. Distinct anatomical locations can permit vaccine access to multiple lymph nodes. In addition, booster immunizations of Dengue vaccines have only been administered after the development of antibody responses in mice, primates and human clinical trials, thirty days or longer. At this time, neutralizing antibodies inhibit the response to the live viral vaccines. It was previously shown that boosting primates one month after primary immunization was less effective than dosing four months after primary immunization. It was speculated that high levels of homologous and heterologous antibodies that circulate after the initial immunization can inhibit viral replication in a second dose. While prolonged (two months or longer) immunization may circumvent this inhibition, it has not been tested whether accelerated immunization regimen with shorter immunization intervals, before the development of potent neutralizing antibody responses may be advantageous. Such a shortened regimen may be an advantage in endemic countries or for travelers, where exposure to Dengue viruses in between the immunizations may put them at risk of disease.

Example 3

In another example, a human clinical trial has been initiated, studying the safety and immunogenicity of two DENVax™ formulations, administered in 0.1 ml either by ID or SC injection. Groups of 12 individuals will be immunized with for example, a low dose DENVax™ formulation ($8\times10^3$ pfu, $5\times10^3$ pfu, $1\times10^4$ pfu and $2\times10^5$ pfu of DENVax™-1, -2, -3 and -4, respectively) or a high dose ($2\times10^4$ pfu, $5\times10^4$ pfu, $1\times10^5$ pfu and $3\times10^5$ pfu of DENVax™-1, -2, -3 and -4, respectively) of DENVax™ ID or SC on Days 0 and 90. Two control groups will be injected SC or ID with phosphate-buffered saline. Patients will be monitored for any adverse events, and for any significant changes in hematological or blood chemistry parameters. Serum samples will be collected to measure vaccine virus replication and neutralizing antibody responses at periodic intervals.

Example 4

Immunogenicity and efficacy of DENVax™ administered intradermally in AG129 mice. In another example, two studies were performed to compare the effect of route of administration on immunogenicity and efficacy of DENVax™ in AG129 mice. In one example, the immunogenicity of monovalent DENVax™-4 (e.g. vaccine against one Dengue virus serotype) was compared in AG129 mice by measuring the neutralizing antibody responses following SC injection under the skin on the back or ID injection into the foot pad using a needle and syringe. Groups of 8 AG129 mice were injected ID or SC with $10^5$ PFU/dose of chimeric DENVax™-4 vaccine in 50 μl and 100 μl final volume, respectively. Six weeks after priming, animals from each treatment group were boosted via the corresponding ID or SC route with $10^5$ PFU of DENVax™-4 or TFA. Mice were bled on Day 31 and 58 and collected sera were pooled to measure neutralizing antibody responses.

Immunization of DENVax™-4 via the ID route elicited a 5-fold higher neutralizing antibody response to DEN-4 after the boost compared to the response induced via the SC route (see for example, FIG. 4). The anti-DEN-4 response elicited by either route of immunization had a marked cross-neutralizing activity against DEN-3 but not against DEN-1 or DEN-2 serotypes. FIG. 4 represents neutralizing antibody responses following primary and secondary immunization of AG129 mice with chimeric DENVax™-4. Mice were bled on Day 31 and 58 and collected sera were pooled to measure neutralizing antibody responses using the plaque reduction assay (PRNT50).

Two weeks after the boost animals from each group were split in to two groups and challenged with $10^6$ PFU of DEN-1 (Mochizuki virus strain) or DEN-2 (New Guinea C strain) viruses. Challenged animals were monitored for clinical signs of disease and survival rates were recorded over a period of 5 weeks. Mice immunized via the ID route showed no signs of disease after DEN-1 challenge (FIG. 5A). In the SC immunized group only one mouse succumbed to infection while the rest of animals had no any apparent signs of infection (FIG. 5B). In contrast, all control animals succumbed to infection by day 13 after DEN-1 challenge (FIG. 5A). Following DEN-2 challenge, all animals immunized with only DENVax™-4 via the route succumbed to infection by day 25 with mean survival time (MST) of 19.5 days as compared to the control (FTA) mice that all succumbed by day 17 (MST=12.5 days) post-challenge (FIG. 5B). In contrast, fifty percent of ID DENVax™-4 immunized mice survived the infection until the end of the 5 week monitoring period (FIG. 5B). FIGS. 5A and 5B represent survivals of DENVax™-4 immune AG129 mice following challenge with DEN-1 (a) or DEN-2 (b) viruses. Challenged animals were monitored for clinical signs of disease and survival rates were recorded over a period of 5 weeks.

In a second study, immunogenicity of tetravalent DENVax™ vaccine administered SC or ID in mice (e.g. AG129) was tested. Groups of AG129 mice, six per group were injected SC or ID with the DENVax™ in 100 μl or 50 μl (final volume), respectively. Mice were immunized with DENVax™ at a 5:4:5:5 ($10^5$ PFU of DENVax™-1, -3 and -4 and $10^4$ PFU of DENVax™-2) dose level of composite chimeric vaccines. All immunized animals received a booster injection of 5:4:5:5 DENVax™ ($10^5$ PFU of DENVax™-1, -3 and -4 and $10^4$ PFU of DENVax™-2) 42 days' post-primary inoculation. Blood samples were collected on days 42 and 56 to measure neutralizing antibody responses to each DEN virus serotype.

As represented in Table 4, both primary and secondary neutralizing antibody responses to all four DEN serotypes were induced. Following the boost, the neutralizing anti-DEN-1, DEN-3 and DEN-4 antibody titers were increased by 2, 5 and 2 fold, respectively in the group of mice injected ID as compared to the SC immunized animals. Neutralizing responses to DEN-2 virus were comparable in both groups. Immunization via the SC route resulted in a profile of dominant neutralizing antibody responses against DEN-1>DEN-2>DEN-3>DEN-4, with neutralizing titers 5120, 1280, 640 and 80, respectively. The hierarchy of neutralizing antibody responses after ID administration had shifted as follows; DEN-1>DEN-3>DEN-2>DEN-4 with neutralizing antibody titers 10240, 3840, 1280 and 160, respectively.

TABLE 4

Comparison of the immunogenicity of tetravalent DENVax ™ bearing the ratio 5:4:5:5 PFU of each composite chimeric virus ($10^5$ PFU of DENVax ™-1, -3 and -4 and $10^4$ PFU of DENVax ™-2) after SC or ID immunization of mice. Blood samples were collected on days 42 and 56 to measure neutralizing antibody responses to each DEN virus serotype.

| DENVax ™ Formulation | Neutralizing Antibody Titers (GMT) | | | | | | | |
|---|---|---|---|---|---|---|---|---|
| | DEN-1 | | DEN-2 | | DEN-3 | | DEN-4 | |
| | Prime | Boost | Prime | Boost | Prime | Boost | Prime | Boost |
| 5:4:5:5/SC | 1920 | 5120 | 3200 | 1280 | 1280 | 640 | 80 | 80 |
| 5:4:5:5/ID | 2560 | 10240 | 1280 | 1280 | 1600 | 3840 | 120 | 160 |

Materials and Methods

Mice: AG129 mice have an "intact" immune system; deficient for the interferon (IFN)-α/β and -γ receptors. Dengue infection has been described for this model. Other studies: pathogenesis, cell tropism, and ADE have also been examined. This model permits challenge with DEN-1 and DEN-2.

Non-human primates: Cynomolgus, rhesus macaques carry virus (viremia), but no disease manifests.

Rapid Dosing Study

Example 5

In one exemplary study, immune responses to tetravalent Dengue vaccines were evaluated for different routes of administration and dosing regimens in the non-human primate model comparing vaccine delivery by conventional needle injection to needle-free administration. The quantifiable endpoints for the nonhuman primate study are i) the route for greatest geometric mean neutralizing antibody titer against each of the four dengue serotypes in non-human primates and ii) the protection from challenge with two of the dengue serotypes.

Two dosing schedules were evaluated in this study—two consecutive doses on Day 0 (at different anatomical sites) were compared to administration of two doses given 60 days apart (0.60). The high dose formulation of the tetravalent formulation (e.g. DENVax™) was used for immunization in this study. This vaccine lot is the same material used for two Phase 1 studies being conducted. The high dose tetravalent formulation vaccine consists of $2 \times 10^4$ pfu of DEN-1, $5 \times 10^4$ pfu of DEN-2, $1 \times 10^5$ pfu DEN-3 and $3 \times 10^5$ pfu DEN-4. The study design for the nonhuman primate study is shown in Table 5.

TABLE 5

Non Human Primate Study

| Group[1] | Treatment | Immunizations | No. of Site(s) for Dosing | Challenge on Day 90, SC route | Route/Method of Administration |
|---|---|---|---|---|---|
| 1 | High dose DENVax | Day 0 | Two (both arms) | 3 animals with wt DENV-2, 3 animals with wt DENV-4 | ID PharmaJet Injector |
| 2 | High dose DENVax | Day 0, Day 60 | One (alternate arms) | 3 animals with wt DENV-2, 3 animals with wt DENV-4 | ID PharmaJet Injector |
| 3 | High dose DENVax | Day 0, Day 60 | One (alternate arms) | 3 animals with wt DENV-2, 3 animals with wt DENV-4 | ID Needle/Syringe |
| 4 | High dose DENVax | Day 0 | Two (both arms) | 3 animals with wt DENV-2, 3 animals with wt DENV-4 | SC PharmaJet Injector |
| 5 | High dose DENVax | Day 0, Day 60 | One (alternate arms) | 3 animals with wt DENV-2, 3 animals with wt DENV-4 | SC PharmaJet Injector |
| 6 | High dose DENVax | Day 0, Day 60 | One (alternate arms) | 3 animals with wt DENV-2, 3 animals with wt DENV-4 | SC Needle/Syringe |
| 7 | PBS | Day 0, Day 60 | One (alternate arms) | 3 animals with wt DENV-2, 3 animals with wt DENV-4 | ID PharmaJet Injector |

Serum samples were collected after each vaccination and wild type dengue virus challenge on Days 0, 3, 5, 7, 10, 12, 14, 53, 64, 67, 88, 91, 93, 95, 97, 99, 101, 102 and 104 to analyze the samples for dengue viremia. Serum samples were also collected on Days 0, 30, 53, 75, 88 and 104 to determine the levels of neutralizing antibodies induced by the tetravalent formulation administered by needle/syringe or the ID injector.

Serum samples were collected at specified intervals during the course of the study. Sera collected on Days 0, Day 30 and Day 88 (pre-boost) have been assayed for neutralizing antibodies to Dengue-1, Dengue-2, Dengue-3 and Dengue-4. The GMT antibody titers are shown below in Table 6.

mals receiving two doses of DENVax™ on Day 0 (one dose in each arm) by either the ID or SC route of administration, displayed a high neutralizing antibody titer to Dengue-1, Dengue-2 and Dengue-4 (Groups 1 and 4). Seroconversion rates by day 30 were 100% for both groups as compared to groups 2 and 3. Both groups maintained high levels of neutralizing antibody responses up to day 88 just prior to virus challenge.

For live attenuated vaccines, vaccine virus replication after immunization is an important measure of vaccine uptake and vaccine safety. Vaccine virus replication in the nonhuman primates was evaluated after the first and second immunization with a live attenuated tetravalent formulation vaccine

TABLE 6

Neutralizing antibody titers to all four dengue serotypes for Days 30, 53, 75 and 88 after one or two immunizations with DENVax.

| Group | Dose Schedule/ Route/Method of Administration/ Treatment | Day 30 Post-Dose 1, Reciprocal GMTs | | | | Day 53 Post-Dose 1, Reciprocal GMTs | | | |
|---|---|---|---|---|---|---|---|---|---|
| | | DEN-1 | DEN-2 | DEN-3 | DEN-4 | DEN-1 | DEN-2 | DEN-3 | DEN-4 |
| 1 | 2 doses (Day 0), PJ ID, DENVax | 80 | 1280 | 127 | 36 | 63 | 1280 | 40 | 13 |
| 2 | 2 doses (Day 0, 60), PJ ID, DENVax | 18 | 14 | 101 | 11 | 32 | 14 | 22 | 10 |
| 3 | 2 doses (Day 0, 60), N/S ID, DENVax | 160 | 36 | 64 | 9 | 45 | 40 | 10 | 5 |
| 4 | 2 doses (Day 0), PJ SC, DENVax | 1016 | 1016 | 403 | 80 | 640 | 1280 | 127 | 45 |
| 5 | 2 doses (Day 0, 60), PJ SC, DENVax | 154 | 1816 | 226 | 64 | 285 | 1280 | 57 | 22 |
| 6 | 2 doses (Day 0, 60), N/S SC, DENVax | 80 | 1140 | 113 | 11 | 80 | 806 | 20 | 28 |
| 7 | 2 doses (Day 0, 60), PJ ID, PBS | 10 | 5 | 6 | 5 | 7 | 5 | 5 | 5 |

Neutralizing antibody titers of <10 are reported as "5". Serum dilutions started at 1:10
Seroconversion (values in parenthesis) is defined as titer >10 over Day 0 < 10 baseline titer or a >4-fold rise in titer if baseline titer on Day 0 was >10.

| Group | Dose Schedule/ Route/Method of Administration/ Treatment | Day 75 Post-Dose 1, Reciprocal GMTs | | | | Day 88 Post-Dose 1, Reciprocal GMTs | | | |
|---|---|---|---|---|---|---|---|---|---|
| | | DEN-1 | DEN-2 | DEN-3 | DEN-4 | DEN-1 | DEN-2 | DEN-3 | DEN-4 |
| 1 | 2 doses (Day 0), PJ ID, DENVax | 40 | 806 | 25 | 25 | 57 | 1016 | 25 | 25 |
| 2 | 2 doses (Day 0, 60), PJ ID, DENVax | 113 | 28 | 63 | 71 | 160 | 90 | 80 | 45 |
| 3 | 2 doses (Day 0, 60), N/S ID, DENVax | 160 | 40 | 57 | 36 | 90 | 101 | 57 | 36 |
| 4 | 2 doses (Day 0), PJ SC, DENVax | 403 | 718 | 90 | 57 | 254 | 640 | 90 | 64 |
| 5 | 2 doses (Day 0, 60), PJ SC, DENVax | 508 | 1810 | 226 | 113 | 403 | 1280 | 127 | 80 |
| 6 | 2 doses (Day 0, 60), N/S SC, DENVax | 143 | 806 | 71 | 57 | 113 | 4064 | 32 | 40 |
| 7 | 2 doses (Day 0, 60), PJ ID, PBS | 5 | 5 | 5 | 5 | 5 | 5 | 5 | 5 |

Neutralizing antibody titers of <10 are reported as a value of "5".
Serum dilutions for analysis started at 1:10.
Results were generated from duplicates or triplicates.
PJ = exemplary PharmaJet needle-free injector,
N/S = needle/syringe;
GMT = Geometric mean titer;
ID = intradermal;
SC = subcutaneous
Data are presented as geometric mean titer (GMT) ± standard error (SE)

All 42 animals in the study were seronegative at the start of the study and displayed no neutralizing antibody titers to any of the four dengue serotypes on Day 0. The results on Day 30 after priming the animals with DENVax™ showed that ani- (DENVax™). Serum samples collected on Days 0, 3, 5, 7, 10, 12, 14 after the first immunization were tested for the presence of viral RNA from the vaccine strains using a qRT-PCR assay (see Table 7).

TABLE 7

DENVax-2 RNA detected in the serum after primary immunization with DENVax.

| | | No. Animals Positive for Viral RNA, DENVax-2 Viral RNA, $\log_{10}$ GE/mL | | | | |
|---|---|---|---|---|---|---|
| Group | Dosing Schedule | Day 5 | Day 7 | Day 10 | Day 12 | Day 14 |
| 1 | 2 doses (Day 0), PJ ID | — | 3/6 (3.9-4.8) | 4/6 (4.5-5.3) | 5/6 (3.9-5.2) | 3/6 (3.8-5.1) |
| 2 | 2 doses (Day 0, 60), PJ ID | — | — | — | — | — |
| 3 | 2 doses (Day 0, 60), N/S ID | — | — | 1/6 (3.8) | 1/6 (3.8) | 1/6 (3.8) |
| 4 | 2 doses (Day 0), PJ SC | 1/6 (3.8) | 5/6 (3.8-5.0) | 5/6 (3.7-5.3) | 1/6 (4.0) | — |
| 5 | 2 doses (Day 0, 60), PJ SC | 1/6 (3.8) | 5/6 (4.5-5.4) | 5/6 (3.8-5.4) | 5/6 (3.2-4.8) | 3/6 (3.7-5.0) |
| 6 | 2 doses (Day 0, 60), N/S SC | — | 3/6 (3.9-5.6) | 4/6 (3.8-5.4) | 3/6 (4.3-5.0) | 2/6 (3.7-4.2) |
| 7 | 2 doses of PBS (Day 0, 60), PJ ID | — | — | — | — | — |

Results are averages from duplicate or triplicate data.
Samples with titers <$\log_{10}$ 3.6 were considered negative.
GE/mL = genome equivalents/mL
N/S = needle/syringe;
PJ = PharmaJet needle-free injector Viral RNA was not detected on Day 0 (pre-vaccination) and Day 3 (post-immunization). For all groups, viral RNA was detected only for the Dengue-2 serotype from day 5 to day 14 post-vaccination after the first immunization. For Groups 1, 3, 5 and 6 endpoint titers were not observed by 14 days post-immunization. Peak titers were observed on Day 10 for Groups 1 and 4, and on Days 7 and 10 for Groups 5 and 6 (Table 7). Viral RNA was not detected for any of the groups after the second immunization evaluated on Days 64 and 67 (4 and 7 days post-dose 2).

On Day 90, three animals from each group were challenged with either wild-type Dengue-2 or Dengue-4 to demonstrate efficacy upon immunization with the tetravalent formulation. Protected animals should exhibit a lack of wild-type Dengue virus infection and replication. Wild-type challenge virus (Dengue-2 and Dengue-4) replication was analyzed for all of the groups after challenge with 10⁶ PFU wild-type Dengue 2 (New Guinea C strain) and Dengue 4 (814669 strain) viruses on Days 91, 93, 95, 97, 99, 101, 102 and 104 (Table 8) Dengue vaccine (e.g. DENVax™): post-challenge viremia Viral RNA of the wild-type challenge viruses was detected only in Group 7 that had received PBS. For Dengue-2, viral RNA was detected in 3 of 3 animals on Days 93 to 97. For Dengue-4, viral RNA was detected in only 1 of 3 animals on Day 95. One important observation of the groups that were immunized with the tetravalent formulation is that no viral RNA for either the Dengue-2 or the Dengue-4 challenge viruses was observed. These results suggested that the tetravalent formulations immunization by any of the dosing schedules tested conferred immune protection against challenge of both Dengue-2 and Dengue-4 wild-type viruses.

Overall, this nonhuman primate study clearly showed that the novel dosing schedule of administering two doses of a tetravalent formulation on Day 0 at two distinct sites (e.g. different arms) induced levels of neutralizing antibodies that were equivalent or higher than those observed for more traditional dosing schedules of delivering the prime and boost immunization 2 to 3 months apart. The onset of the immune responses was more rapid for the groups that received two doses on Day 0 and long lasting. The application of the

TABLE 8

Protection of DENVax-immunized NHPs from wt DENV challenge.

| Vaccination & Challenge Regimen | | Pre-Challenge Antibody Titers (GMT), Day 88 | | | | Post-Challenge Viremia ($\log_{10}$ GE/mL) | | |
|---|---|---|---|---|---|---|---|---|
| | | DEN-1 | DEN-2 | DEN-3 | DEN-4 | Day 3 | Day 5 | Day 7 |
| 2 doses on Day 0, PJ ID, DENVax | DENV-2 DENV-4 | 57 | 1016 | 25 | 25 | — | — | — |
| 2 doses on Day 0, 60, PJ ID, DENVax | DENV-2 DENV-4 | 160 | 90 | 80 | 45 | — | — | — |
| 2 doses on Day 0, 60, N/S ID, DENVax | DENV-2 DENV-4 | 90 | 101 | 57 | 36 | — | — | — |
| 2 doses on Day 0, PJ SC, DENVax | DENV-2 DENV-4 | 254 | 640 | 90 | 64 | — | — | — |
| 2 doses on Day 0, 60, PJ SC, DENVax | DENV-2 DENV-4 | 403 | 1280 | 127 | 80 | — | — | — |
| 2 doses on Day 0, 60, N/S SC, DENVax | DENV-2 DENV-4 | 113 | 4064 | 32 | 40 | — | — | — | needle-free ID or SC injector enhanced the immune responses such that higher titers were observed.

Example 6

AG129 Mouse Studies on Rapid Immunization

In another exemplary study, novel dosing schedules were designed that explore either administration of two vaccine doses at two distinct sites on a single occasion or shorter dosing intervals between two doses of vaccine which will enhance compliance of vaccinated subjects to return for the second immunization. Standard Dengue vaccines developed previously typically require three doses over the course of a year to achieve robust multivalent Dengue immune responses. With respect to vaccination schedules presented herein, response was evaluated for immunization occurring in at least two anatomical two sites, and administering, in certain embodiments, a full dose (see Table 9) at each site intradermally. This protocol was performed in part to activate immune cells and antigen presenting cells in two different lymph nodes on Day 0 to induce higher levels and more robust dengue-specific immune responses compared to administering two doses intradermally 7, 14 or 42 days apart. In one study two routes of administration were compared, SC and ID routes using a conventional 42-day interval between vaccinations. The mice were immunized with a low dose formulation of a tetravalent formulation (DENVax™; 3:3:3:3 ratio of each of the serotypes) which consisted of $10^3$ PFU of each Dengue-1, -2, -3, and -4 (e.g. DENVax™-1, -2, -3 and -4) in a 0.05 mL volume given via the intradermal route (in the foot pad). The in live portion of this study was conducted prior to initiation of this contract. The study design is shown in Table 9 below.

TABLE 9

Study design for AG129 mouse study DEN-012.

| Groups | Dose | Number of Immunizations/Route | Number of Animals |
|---|---|---|---|
| A | DENVax ™ (3:3:3:3) | 1 (day 0)/ID | 6 |
| B | DENVax ™ (3:3:3:3) | 2 (day 0)/ID, giving a full dose into each of two footpads | 6 |
| C | DENVax ™ (3:3:3:3) | 2 (7 days apart)/ID | 6 |
| D | DENVax ™ (3:3:3:3) | 2 (14 days apart)/ID | 6 |
| E | DENVax ™ (3:3:3:3) | 2 (42 days apart)/ID | 6 |
| F | FTA (negative control group) | 2 (14 days apart)/ID | 6 |
| G | DENVax ™ (3:3:3:3) | 2 (42 days apart)/SC | 6 |

The neutralizing antibody titers to Dengue 1-4 present in the collected mouse sera were determined by a microneutralization assay. Sera were collected at specified time points throughout the study and the longevity of the immune responses was studied by maintaining the study groups until Day 160 (longer than 5 months after study start). The results obtained from sera collected on Days 28 and 56 post-immunization are illustrated in Table 10.

TABLE 10

Neutralizing antibody titers (GMTs) to DEN-1, -2, -3 and -4

| | | GMT, Day 28 | | | |
|---|---|---|---|---|---|
| Group | Treatment Groups | DEN-1 | DEN-2 | DEN-3 | DEN-4 |
| A | 1 (day 0)/ID | 400 | 100 | 200 | 40 |
| B | 2 (day 0)/ID, giving a full dose into each of two footpads | 800 | 200 | 800 | 160 |
| C | 2 (42 days apart)/ID | 400 | 100 | 200 | 40 |
| D | 2 (14 days apart)/ID (negative control) | <20 | <20 | <20 | <20 |

| | GMT, Day 56 | | | |
|---|---|---|---|---|
| Group | DEN-1 | DEN-2 | DEN-3 | DEN-4 |
| A | 800 | 200 | 400 | 40 |
| B | 3200 | 400 | 1600 | 160 |
| C | 1600 | 200 | 800 | 40 |
| D | <20 | <20 | <20 | <20 |

In previous studies, a conventional dosing schedule of priming animals was used on Day 0 and then administering a booster vaccination on Day 42 to evaluate the immune responses for the tetravalent dengue vaccine. Both prime and boost vaccinations were administered by the subcutaneous (SC) route. This dosing schedule was included in the study for comparison to the novel dosing schedules. Initially, one study (represented in Table 10) compared the SC and ID routes of administration using the conventional dosing interval of giving two doses 42 days apart. The results indicate that there is no significant difference between the SC and ID routes with respect to neutralizing antibodies induced in this mouse model. This study further explored whether two doses administered on Day 0 at two anatomical sites (one dose into each of two foot pads) could induce neutralizing antibody levels similar to the standard dosing schedule (2 doses 42 days apart) described above. The results show that immunization on Day 0 at two sites each, with a full dose of a tetravalent formulation of DENVax™, via the ID route induced neutralizing antibody levels to all four dengue serotypes that are equivalent in magnitude to the conventional dosing schedule. The effect of a single vaccine dose administered by the ID route was also studied (Group A). Administration of a single dose of DENVax™ on Day 0 resulted in antibody responses that trended slightly lower compared to two doses on Day 0 (compare Groups A and B). Increasing the interval between the two doses from 7 to 42 days did increase antibody responses beyond the levels observed. Evaluation of the longevity of the Dengue immune response revealed that neutralizing antibody titers to all four dengue serotypes remained at high levels at Day 160 post-immunization independent of route of administration and dosing schedule (data not shown).

Overall, the results suggested that the intradermal route of administration induces neutralizing antibody levels equivalent to those observed for the subcutaneous route. Further, the administration of two doses on Day 0 at two different sites by the ID route induced a robust neutralizing antibody response equivalent to conventional dosing schedules. The antibody responses induced were long lasting and decreased only slightly. The animals did not display increased morbidity and mortality. This study demonstrated that administration of two vaccine doses at two distinct sites is a viable option for immunization as the resulting antibody titers and duration of immune responses are equivalent in magnitude to those resulting from two doses given 42 days apart. These dosing regimens will be beneficial for travelers to dengue endemic regions and others in need of fast protection from dengue virus exposure.

Example 7

Another Rapid Immunization Study in AG129 Mice

The objective of this study was to determine whether administering two doses at two sites ID on Day 0 will induce higher levels and more robust Dengue-specific immune responses compared to administering two doses ID 42 days apart. The hypothesis to be tested was whether administration of a full vaccine dose to each of two sites intradermally will activate immune cells and antigen presenting cells that traffic to two different lymph nodes, thereby reducing interference between the four DENVax™ vaccine components. The design for this AG129 mouse study is shown below in Table 11.

TABLE 11

Design of Example 7 AG129 mouse study

| Group | Dose | Number of Immunizations/Route | Number of Animals |
|---|---|---|---|
| 1 | DENVax ™ 3:3:3:3 | 2 doses (day 0)/ID using both footpads | 8 |
| 2 | DENVax ™ 3:3:3:3 | 2 doses (day 0, day 42)/ID using both footpads | 8 |
| 3 | DENVax ™ 4:3:4:5 | 2 doses (day 0)/ID using both footpads | 8 |
| 4 | DENVax ™ 4:3:4:5 | 2 doses (day 0, day 42)/ID using both footpads | 8 |
| 5 | FTA (negative control group) | 2 doses (day 0)/ID using both footpads | 8 |

In this exemplary method, two different vaccine dose levels (low and medium dose), were used for immunization using the novel dosing schedule of administering two doses on Day 0 compared to two doses 42 days apart. The mice were dosed with either a low dose formulation of DENVax™ (3:3:3:3) which consisted of $10^3$ PFU of each of DENVax™-1, -2, -3, and 4 in a 0.05 mL volume given via the intradermal route (in the foot pad) or a medium dose formulation of DENVax™ (4:3:4:5) which contained $10^4$ PFU of DENVax™-1, $10^3$ PFU of DENVax™-2, $10^4$ PFU of DENVax™-3, and $10^5$ PFU of DENVax™-4 in a 0.05 mL volume. On Day 0 all mice were immunized and Groups 2 and 4 were boosted on Day 42. Sera for antibody analysis were collected on Days 14, 41 and 56 post-primary vaccination and analyzed using a plaque reduction microneutralization assay to determine the neutralizing antibody levels to all four dengue serotypes. Immunogenicity results obtained from pooled mouse serum samples are shown in Table 12.

TABLE 12

Neutralizing antibody titers for AG129 mouse study DEN-013

| | Reciprocal Neutralizing Antibody Titers (PRNT50) | | | | | | | | | | | |
|---|---|---|---|---|---|---|---|---|---|---|---|---|
| | 14 Days p.i.[1] | | | | 41 Days p.i.[1] | | | | 56 Days p.i.[1] | | | |
| Group | DEN-1 | DEN-2 | DEN-3 | DEN-4 | DEN-1 | DEN-2 | DEN-3 | DEN-4 | DEN-1 | DEN-2 | DEN-3 | DEN-4 |
| 1 | 320 | 160 | 80 | 20 | 640 | 640 | 640 | 80 | 800 | 1600 | 800 | 40 |
| 2 | 320 | 320 | 40 | 20 | 640 | 640 | 320 | 80 | 800 | 800 | 400 | 40 |
| 3 | 640 | 80 | 80 | 40 | 2560 | 640 | 1280 | 160 | 3200 | 800 | 800 | 40 |
| 4 | 320 | 80 | 40 | 20 | 320 | 160 | 640 | 80 | 1600 | 800 | 800 | 80 |
| 5 | 20 | 20 | 20 | 20 | 20 | 20 | 20 | 20 | 20 | 20 | 20 | 20 |

[1]p.i.—post-infection

In this example, immunization with either the low or medium dose tetravalent vaccine (e.g. DENVax™) formulation induced neutralizing antibodies to all four dengue serotypes at the early check on Day 14 post-vaccination, independent of administration of one vs. two doses on Day 0. The medium dose DENVax™ formulation induced slightly higher neutralizing antibody titers by Day 28 for Groups 1 and 3 particularly for DEN-1 and DEN-3, that received two doses on Day 0 compared to groups that received only a single dose on Day 0 (Groups 2 and 4). The antibody titers obtained from sera collected on Day 56 indicate that the neutralizing antibody responses persisted and did not wane regardless of whether the animals were boosted on Day 42 or received vaccine only on Day 0. The results obtained in this study further support the application of the novel dosing schedule of administering two doses on Day 0 at two distinct sites (e.g. immunologically).

TABLE 13

Neutralizing antibody titers for AG129 mouse study DEN-013

| | | | DEN-1 | | DEN-2 | | DEN-3 | | DEN-4 | |
|---|---|---|---|---|---|---|---|---|---|---|
| | | | Day 28 | Day 56 | Day 28 | Day 56 | Day 28 | Day 56 | Day 28 | Day 56 |
| Study 1 | 3:3:3:3 | 2 (d0) | 640 | 800 | 320 | 1600 | 160 | 800 | 20 | 40 |
| | | 2 (d0, 42) | 320 | 800 | 320 | 800 | 160 | 400 | 40 | 40 |

TABLE 13-continued

Neutralizing antibody titers for AG129 mouse study DEN-013

| | | | DEN-1 | | DEN-2 | | DEN-3 | | DEN-4 | |
|---|---|---|---|---|---|---|---|---|---|---|
| | | | Day 28 | Day 56 | Day 28 | Day 56 | Day 28 | Day 56 | Day 28 | Day 56 |
| | 4:3:4:5 | 2 (d0) | 1280 | 3200 | 320 | 800 | 640 | 800 | 80 | 40 |
| | | 2 (d0, 42) | 320 | 1600 | 160 | 800 | 80 | 800 | 40 | 80 |
| | FTA | 2 (d0) | 40 | 20 | <20 | 20 | 20 | 20 | <20 | 20 |
| | NMS | | 20 | 20 | 20 | 20 | 20 | 20 | <20 | 20 |
| Study 2 | 3:3:3:3 | 2 (d0) | 800 | 3200 | 200 | 400 | 800 | 1600 | 160 | 160 |
| | | 2 (d0, 42) | 400 | 1600 | 100 | 200 | 200 | 800 | 40 | 40 |
| | FTA | 2 (d0, 14) | 20 | <20 | <20 | <20 | 20 | 20 | 20 | <20 |
| | NMS | | 20 | 20 | 40 | 20 | 20 | 20 | 20 | 20 |

ELISPOT dengue virus neutralizing titers calculated using 50% NMS cutoff at a starting dilution of 1:20. Serum from individual animals within a group were pooled and tested in triplicate.

Example 8

FIGS. 9A-9D represent graphs comparing neutralizing antibody titers achieved in non-human primates after immunization with tetravalent DENVax containing DENVax-1 ($1\times10^5$ pfu); DENVax-2 ($1\times10^4$ pfu); DENVax-3 ($1\times10^5$ pfu); DENVax-4 ($1\times10^6$ pfu). Two groups were vaccinated with the needle-free PharmaJet device via the subcutaneous route either twice on the same day (0,0) or once on day 0 and again on day 60 (0,60). Serum was analyzed for presence of antibodies on days 0, 30, 53, 75 and 88, and the detection of antibodies against four dengue serotypes were analyzed (DEN-1, DEN-2, DEN-3, DEN-4).

In another example, seronegative human subjects were immunized with two doses of a tetravalent formulation of DENVax containing DENVax-1 ($1\times10^4$ pfu); DENVax-22 ($1\times10^3$ pfu); DENVax3 ($1\times10^4$ pfu); DENVax-4 ($1\times10^5$ pfu). The route of immunization was subcutaneous or intradermal, and the vaccinations were given 90 days apart. Antibody levels against each of the dengue serotypes were analyzed on days 0, 30, 60, 90 and 120. The vaccine induced neutralizing antibodies to all four serotypes. However, the levels of seroconversion were different when comparing the routes of immunization. Overall, the intradermal route of immunization produced appeared to be more "balanced" immune responses in this study, with the levels of antibodies being more equivalent as compared to the subcutaneous route.

Figure 10A:
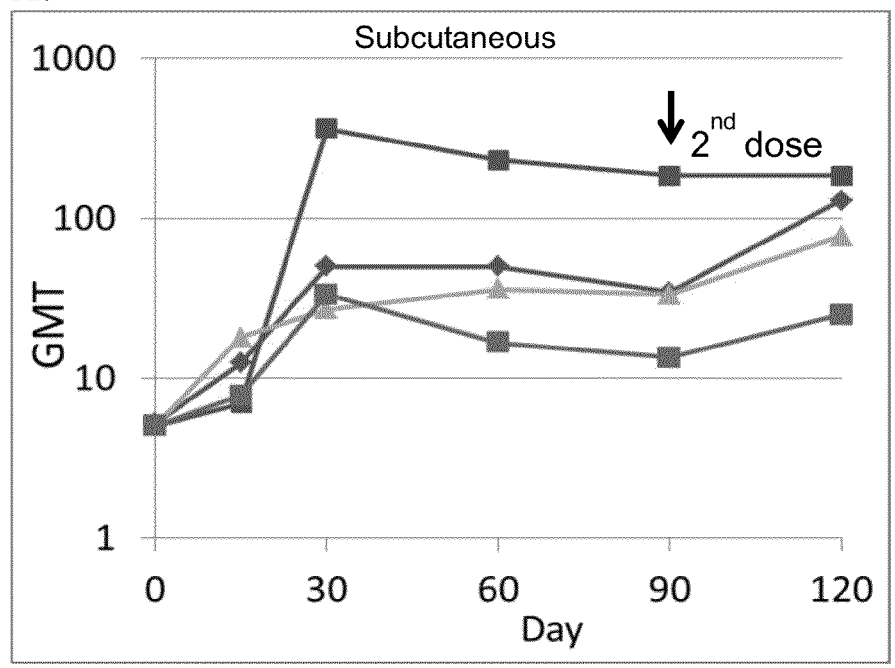
FIGS. 10A-10B represent data obtained from a human clinical trial. Seronegative humans (humans demonstrating little to no antibodies to dengue virus serotypes at the onset of the trial) were given two doses of a tetravalent serotype formulation of dengue vaccine either subcutaneously or intradermally (day 0 and day 90). Antibody levels against each of the dengue serotypes were analyzed on days 0, 30, 60, 90 and 120.
Figure 10B:
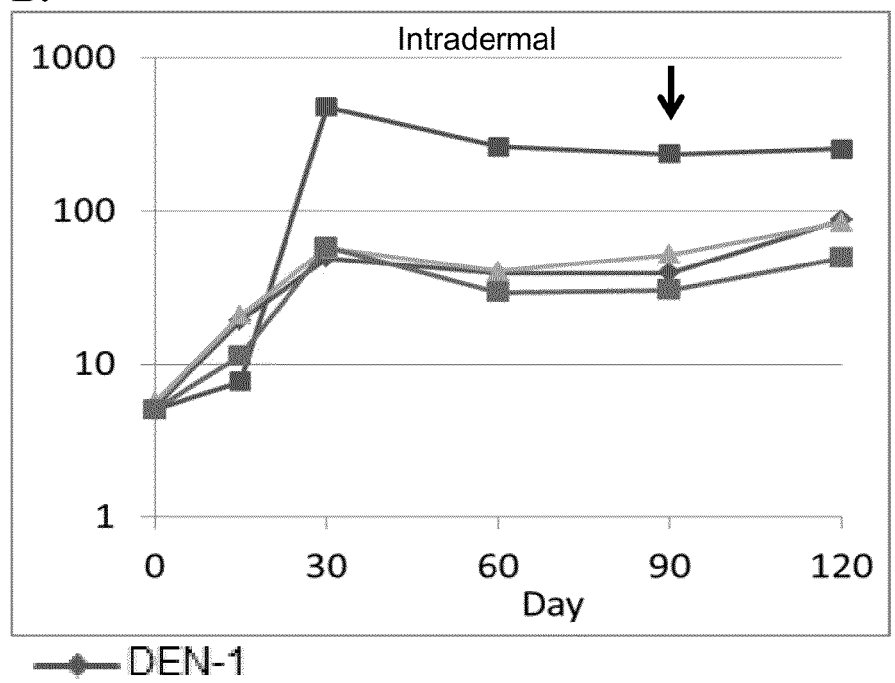
Figure 11A:
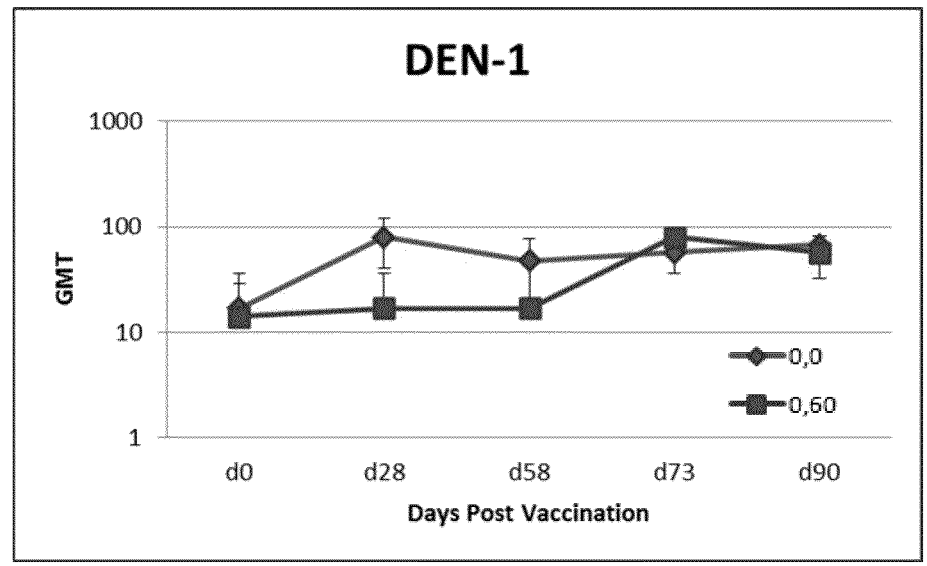
FIGS. 11A-11D represent a graph comparing neutralizing antibody titers achieved in non-human primates after subcutaneous immunization with a tetravalent serotype dengue vaccine. Two groups were vaccinated either twice on the same day (0,0) or once on day 0 and again on day 60 (0,60). Serum was analyzed for presence of antibodies on days 0, 28, 58, 73 and 90, and the detection of antibodies against all four dengue serotypes were analyzed (DEN-1, DEN-2, DEN-3, DEN-4).
Figure 11B:
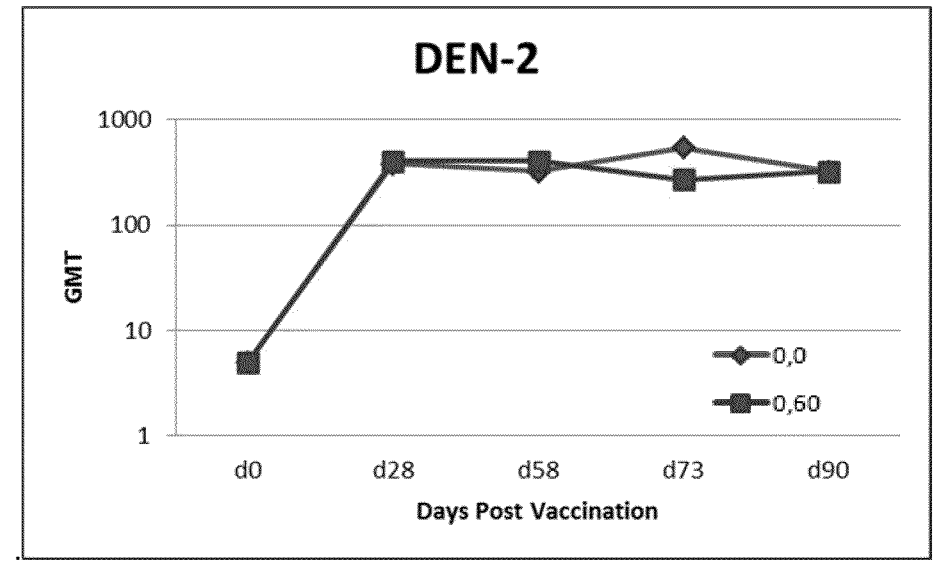
Figure 11C:
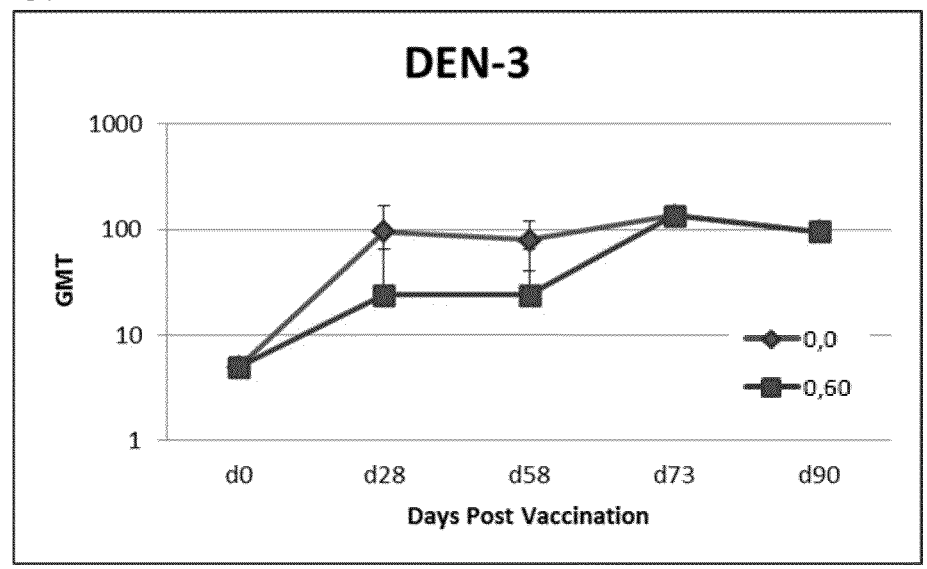
Figure 11D:
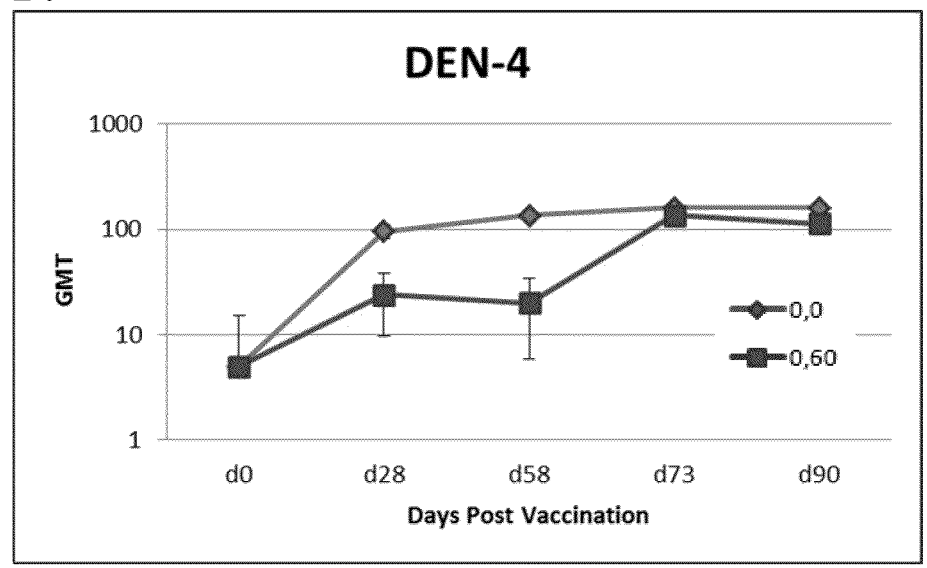

FIG. 10 represents the data obtained from a human clinical trial in Colombia. Seronegative humans were given two doses of a tetravalent formulation of DENVax containing DENVax-1 ($1\times10^4$ pfu); DENVax-2 ($1\times10^3$ pfu); DENVax-3 ($1\times10^4$ pfu); DENVax-4 ($1\times10^5$ pfu) subcutaneously or intradermally. Antibody levels against each of the dengue serotypes were analyzed on days 0, 30, 60, 90 and 120.

In this exemplary method, non-human primates were immunized with two doses of a tetravalent vaccine (e.g. DENVax™ DENVax-1: $2\times10^4$ pfu, DENVax-2: $5\times10^4$ pfu, DENVax-3: $1\times10^5$ pfu, DENVax-4: $3\times10^6$ pfu) either simultaneously on Day 0, or two separate doses on days 0 and 60. The vaccine induced neutralizing antibodies to all four Dengue serotypes. By day 90 post vaccination, the neutralizing antibody titers of the two groups were relatively equal (FIG. 11). However, the kinetics of the immune response was more rapid in the group which received two immunizations on day 0. The results obtained in this study further support the application of the novel dosing schedule of administering two doses on Day 0 at two immunologically distinct sites.

FIG. 11 represents a graph comparing neutralizing antibody titers achieved in non-human primates after subcutaneous immunization with tetravalent DENVax containing DENVax-1 ($1\times10^5$ pfu); DENVax-2 ($1\times10^4$ pfu); DENVax-3 ($1\times10^5$ pfu); DENVax-4 ($1\times10^6$ pfu). Two groups were vaccinated either twice on the same day (0,0) or once on day 0 and again on day 60 (0,60). Serum was analyzed for presence of antibodies on days 0, 28, 58, 73 and 90, and the detection of antibodies against four dengue serotypes were analyzed (DEN-1, DEN-2, DEN-3, DEN-4).

All of the COMPOSITIONS and METHODS disclosed and claimed herein can be made and executed without undue experimentation in light of the present disclosure. While the compositions and methods have been described in terms of preferred embodiments, it is apparent to those of skill in the art that variations maybe applied to the COMPOSITIONS and METHODS and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

What is claimed is:

1. A method for inducing neutralizing antibodies in a subject against three or more dengue virus serotypes, comprising, administering two or more doses of a single immunogenic composition of a mixture of three or more different dengue-dengue chimeras of live, attenuated dengue viruses to the subject at two or more anatomical locations on the same day, inducing neutralizing antibodies in the subject against three or more dengue virus serotypes.

2. The method of claim 1, further comprising administering at least one additional booster administration of an immunogenic composition of live, attenuated dengue viruses 1 to 180 days after the same day administrations of the immunogenic composition claim 1.

3. The method of claim 1, wherein the single immunogenic composition comprises a predetermined ratio of live, attenuated dengue viruses representing the three or more dengue virus serotypes in the single composition.

4. The method of claim 1, wherein the single immunogenic composition comprises equivalent ratios of live, attenuated dengue viruses representing the three or more dengue virus serotypes in the single composition.

5. The method of claim 2, wherein the immunogenic composition used for at least one additional booster administration is identical to the single immunogenic composition used for the same day administrations of the immunogenic composition of claim 1.

6. The method of claim 2, wherein the immunogenic composition used for at least one additional booster administration is different than the single immunogenic composition used for the same day administrations of claim 1 and comprises pre-determined concentrations of one or more monovalent live, attenuated dengue virus serotypes.

7. The method of claim 6, wherein the pre-determined concentration of dengue virus serotypes includes a higher concentration of one or more live, attenuated dengue virus serotypes than the single immunogenic composition used for the same day administrations of claim 1.

8. The method of claim 7, wherein the higher concentration is 2 to 100,000 fold greater concentration than used in the single immunogenic composition according to claim 1.

9. The method of claim 1, wherein the two or more anatomical sites comprise different anatomical locations using the same mode of administration.

10. The method of claim 1, wherein the two or more anatomical sites comprise different anatomical locations using different modes of administration.

11. The method of claim 1, wherein modes of administration of the single immunogenic composition comprise subcutaneous (SC), intradermal (ID), or intramuscular (IM).

12. The method of claim 2, wherein at least one additional booster is administered to the subject within 30 days after the same day single immunogenic composition administrations.

13. The method of claim 1, further comprising administering at least one immunogenic agent to the subject.

14. The method of claim 1, wherein the single immunogenic composition comprises all four dengue virus serotypes.

* * * * *